United States Patent
Zhou et al.

(10) Patent No.: US 11,918,957 B2
(45) Date of Patent: Mar. 5, 2024

(54) AFFINITY MEMBRANE AND METHOD OF PREPARATION

(71) Applicant: Donaldson Company, Inc., Bloomington, MN (US)

(72) Inventors: Jinxiang Zhou, Greenville, SC (US); Graham Temples, Greenville, SC (US); Daniel Henn, Greenville, SC (US)

(73) Assignee: Donaldson Company, Inc., Bloomington, MN (US)

( * ) Notice: Subject to any disclaimer, the term of this patent is extended or adjusted under 35 U.S.C. 154(b) by 367 days.

(21) Appl. No.: 16/711,339

(22) Filed: Dec. 11, 2019

(65) Prior Publication Data
US 2020/0188859 A1    Jun. 18, 2020

Related U.S. Application Data

(60) Provisional application No. 62/778,412, filed on Dec. 12, 2018.

(51) Int. Cl.
  *B01D 67/00* (2006.01)
  *B01D 69/10* (2006.01)
  (Continued)

(52) U.S. Cl.
  CPC ..... *B01D 67/0088* (2013.01); *B01D 67/0093* (2013.01); *B01D 69/105* (2013.01);
  (Continued)

(58) Field of Classification Search
  None
  See application file for complete search history.

(56) References Cited

U.S. PATENT DOCUMENTS

| | | | |
|---|---|---|---|
| 4,361,484 A | | 11/1982 | Larsson et al. |
| 4,693,985 A | * | 9/1987 | Degen .............. G01N 33/54353 |
| | | | 210/198.2 |

(Continued)

FOREIGN PATENT DOCUMENTS

| | | | |
|---|---|---|---|
| EP | 1352957 A1 | 10/2003 | |
| EP | 1445260 A1 * | 8/2004 | .............. C07K 1/04 |

(Continued)

OTHER PUBLICATIONS

Miron et al., "A simplified method for the preparation of succinimidyl carbonate polyethylene glycol for coupling proteins", Bioconjugate Chem. vol. 4, No. 6, 568-569, Jan. 21, 1993.

(Continued)

*Primary Examiner* — Krishnan S Menon
(74) *Attorney, Agent, or Firm* — Mueting Raasch Group

(57) ABSTRACT

A method for preparing an adsorptive media for binding biologic molecules comprising immersing a macroporous support in a first solution of a coupling reagent in a solvent solution for attachment of said coupling reagent to form coupling groups; and, immersing said macroporous support in an incubating solution selected from the group consisting of ligand, nucleotide, oligonucleotide, peptide, polypeptide, protein, and enzyme solutions having an affinity to a biologic target molecule to couple one of said ligands, nucleotides, oligonucleotides, peptides, polypeptides, proteins, and enzymes to at least a portion of said coupling groups of said macroporous support for binding with said biologic target molecule when exposed to said macroporous support.

19 Claims, 9 Drawing Sheets

(51) Int. Cl.
    B01D 69/14      (2006.01)
    B01D 71/10      (2006.01)
    B01J 20/28      (2006.01)
    C07K 1/22       (2006.01)
(52) U.S. Cl.
    CPC .......... B01D 69/144 (2013.01); B01D 71/10
            (2013.01); B01J 20/28033 (2013.01); C07K
                    1/22 (2013.01); B01D 2323/16 (2013.01)

(56)                  References Cited

U.S. PATENT DOCUMENTS

| | | |
|---|---|---|
| 4,772,635 A | 9/1988 | Mitschker et al. |
| 5,071,909 A | 12/1991 | Pappin |
| 5,260,373 A | 11/1993 | Profy |
| 5,330,687 A | 7/1994 | Rieke |
| 5,543,054 A | 8/1996 | Charkoudian |
| 5,595,879 A | 1/1997 | Utermohlen |
| 5,683,916 A | 11/1997 | Goffe et al. |
| 5,766,908 A | 6/1998 | Klein |
| 7,833,723 B2 | 11/2010 | Bian |
| 2008/0179248 A1 | 7/2008 | Axen et al. |
| 2011/0117626 A1 | 5/2011 | Komkova et al. |
| 2011/0120947 A1 | 5/2011 | Faber |
| 2011/0147292 A1 | 6/2011 | Demmer et al. |
| 2012/0074068 A1 | 3/2012 | Hoerl et al. |
| 2014/0238935 A1 | 8/2014 | Komkova et al. |
| 2016/0115193 A1 | 4/2016 | Herigstad et al. |
| 2018/0094024 A1 | 4/2018 | Forss et al. |
| 2018/0297023 A1 | 10/2018 | Ragheb et al. |
| 2020/0047086 A1 | 2/2020 | Zhou |
| 2023/0010637 A1 | 1/2023 | Zhou et al. |
| 2023/0028254 A1 | 1/2023 | Zhou et al. |

FOREIGN PATENT DOCUMENTS

| | | |
|---|---|---|
| EP | 1445260 A1 | 8/2004 |
| EP | 2942353 B1 | 11/2015 |
| JP | H11-503005 A | 3/1999 |
| JP | 2004-041341 A | 2/2004 |
| JP | 2009-522580 A | 6/2009 |
| JP | 2009-262078 A | 11/2009 |
| WO | 80/02805 | 12/1980 |
| WO | 2004074471 A1 | 9/2004 |
| WO | 2011104307 A2 | 9/2011 |
| WO | 2017176522 A1 | 10/2017 |
| WO | 2017/069254 A | 7/2018 |
| WO | 2020123714 A1 | 6/2020 |
| WO | 2022104197 A1 | 5/2022 |
| WO | 2023287718 A1 | 1/2023 |
| WO | 2023287733 A1 | 1/2023 |

OTHER PUBLICATIONS

Cha et al., "Enzymatic activity on a chip: The critical role of protein orientation", Proteomics 5, 416-419, 2005.
Gautam et al., "Immobilization of hydrophobic peptidic ligands to hydrophilic chromatographic matrix: A preconcentration approach", Analytical Biochemistry 423 (2012) 202-209, Jan. 27, 2012.
Johnsson et al., "Immobilization of proteins to a carboxymethyldextran-modified gold surface for biospecific interaction analysis in surface plasmon resonance sensors", Analytical Biochemistry 198, 268-277, 1991.
Wakaskar et al., "Peripherally cross-linking the shell of core-shell polymer micelles decreases premature release of physically loaded combretastatin A4 in whole blood and increases its mean residence time and subsequent potency", Pharm Res. 32(3): 1028-1044, Mar. 2015.
Seo et al., "Regioselective covalent immobilization of recombinant antibody binding proteins A, G, and Protein L for construction of antibody arrays", Journal of the American Chemical Society, 135, 8973-8980, Jun. 10, 2013.

International Search Report and Written Opinion for PCT/US2019/065805.
Mustafaogle et al. "Antibody purification via affinity membrane chromatography method utilizing nucleotide binding site targeting with a small molecule" Analyst, 2016, 141, 6571-6582. Nov. 10, 2016.
Barbosa et al. "Heterofunctional Supports in Enzyme Immobilization: From Traditional Immobilization Protocols to Opportunities in Tuning Enzyme Properties" Biomacromolecules 2013, 14, 2433-2462. Jul. 3, 2013.
Acikara et al. "Affinity Chromatography and Importance in Drug Discovery" in book Column Chromatograph, Apr. 10, 2013.
Cellulose Swelling by Aprotic and Protic Solvents: What are the Similarities and Differences?; Ludmila C. Fidale, Naiara Ruiz, Thomas Heinze, Omar A. El Seoud; Macromol. Chem. Phys. 2008, 209, 1240-1254.
Membrane adsorbers as purification tools for monoclonal antibody purification; Cristiana Boi; Abstract, Journal of Chromatography B, vol. 848, Issue 1, Mar. 15, 2007, pp. 19-27.
Maximizing binding capacity for protein A chromatography; Ghose S., Zhang J., Conley L., Caple R., Williams KP., Cecchini D .; Absract, Biotechnol Prog. Nov.-Dec. 2014; 30(6): 1335-40.
Barroso et al., "Preparation and characterization of a cellulose affinity membrane for human immunoglobulin G (IgG) purification", 2010, Journal of Membrane Science, 348:224-230. Available online Nov. 10, 2009.
Ma, et al., "Electrospun regenerated cellulose nanofiber affinity membrane functionalized with protein A/G for IgG purification", 2008, Journal of Membrane Science, 319:23-28. Available online Mar. 30, 2008.
Batzer et al., "Enhanced evolutionary PCR using oligonucleotides with inosine at the 3'-terminus," Nucleic Acid Research, Sep. 25, 1991, vol. 19, No. 18, pp. 5081.
International Preliminary Report on Patentability in PCT/US2019/065805, dated Jun. 8, 2021, 10 pages.
International Preliminary Report on Patentability in PCT/US2021/059363, dated May 16, 2023, 6 pages.
International Search Report and Written Opinion in PCT/US2021/059363, dated Feb. 4, 2022, 8 pages.
International Search Report and Written Opinion in PCT/US2022/036711, dated Dec. 15, 2022, 16 pages.
International Search Report and Written Opinion in PCT/US2022/036740, dated Dec. 23, 2022, 16 pages.
Invitation to Pay Additional Fees in PCT/US2022/036740, dated Oct. 27, 2022, 12 pages.
McGettrick et al., "Dye-Ligand Affinity Chromatography," In: Cutler, P. (eds) Protein Purification Protocols. Methods in Molecular Biology, Humana Press, Dec. 12, 2003, vol. 244, pp. 151-157.
Micklefield, Jason, "Backbone Modification of Nucleic Acids: Synthesis, Structure and Therapeutic Applications," Current Medicinal Chemistry, Aug. 1, 2001, vol. 8, No. 10, pp. 1157-1179.
Ohtsuka et al., "An alternative approach to deoxyoligonucleotides as hybridization probes by insertion of deoxyinosine at ambiguous codon positions," Journal of Biological Chemistry, Mar. 10, 1985, vol. 260, No. 5, pp. 2605-2608.
Rossolini et al., "Use of deoxyinosine-containing primers vs degenerate primers for polymerase chain reaction based on ambiguous sequence information," Molecular and Cellular Probes, Apr. 1994, vol. 8, No. 2, pp. 91-98.
Stellwagen et al., "Dye affinity chromatography," Current Protocols in Protein Science, May 1, 2001, Chapter 9, Unit 9.2.
U.S. Appl. No. 17/742,956, filed May 12, 2022, 24 pages.
U.S. Appl. No. 17/862,364, filed Jul. 11, 2022, 55 pages.
U.S. Appl. No. 18/036,732, filed May 12, 2023, 19 pages.
Boi et al., "Membrane adsorbers as purification tools for monoclonal antibody purification," Journal of Chromatography B, Mar. 2007, vol. 848, No. 1, pp. 19-27.
Ghose et al., "Maximizing binding capacity for protein A chromatography," Biotechnology Progress, Nov.-Dec. 2014, vol. 30, No. 6, pp. 1335-1340.

* cited by examiner

AFFINITY MEMBRANE AND METHOD OF PREPARATION

GOVERNMENT FUNDING

This invention was made with government support under GM125429 awarded by the National Institutes of Health. The government has certain rights in the invention.

BACKGROUND OF THE INVENTION

1) Field of the Invention

The present invention relates to a membrane for purifying biologics such as proteins, polypeptides, peptides, polynucleotides, nucleotides, viral vectors, and vaccines using affinity separation methods, and more particularly, to a membrane and a method of preparing a membrane that provides a high binding capacity for biologics at short residence times.

2) Description of Related Art

Biologics including monoclonal antibodies (mAbs) are the principal components of many therapeutic regimens for chronic conditions such as cancers, autoimmune disorders, cardiovascular diseases, and many orphan diseases. However, biologics are among the most expensive drugs. For example, recent reports indicate that the cost for mAb research, development, and production account for ~35% of the drug price. Drug research is becoming more expensive over time, with the R&D cost to develop an FDA approved drug doubling every 9 years. In addition, the industry is moving towards small batch production as a strategy to reduce market uncertainty due to increasing competition. Particularly, demand is growing for small-batch production runs due to competition and emerging markets, such as personalized medicine and orphan drugs. However, costs per dose for small-batch production of biologics can be 10 times higher than large-scale production. Technologies that can rapidly and efficiently purify biologics will contribute to improved human health by enabling the production of affordable medications.

A major drawback of resin-based columns is that binding capacity decreases as flow rate increases (shorter residence time). Long residence times must be used to attain high capacities due to slow mass transfer of proteins through the small pore structures of the resins. Typical resin chromatography products take 6 min residence time or longer to achieve optimum binding capacity. Such long residence time results in very low productivity and sometimes, it leads to product degradation.

For example, the Protein A ligand has been used routinely as a platform technology for mAb capture in the industry due to its high affinity towards the Fc region of antibodies. Despite the strong preference to use Protein A based products for mAb purification, leading Protein A resin chromatography products have capacities of 60-80 mg mAb/mL at 6 min residence time. Their capacities will drop to 18-30 mg/mL at 1 to 2 min residence times. As such, there are currently no Protein A chromatography products in the market (or known to be under development) have >40 mg/mL binding capacity at 6 seconds residence time or less. Similarly, highly productive affinity chromatography products for other biologics, such as plasmid DNA, messenger RNA, viral vectors, virus particles, virus-like particles, native proteins, recombinant proteins, and endotoxins, are also not available.

Membrane chromatography addresses this problem and offers an alternative to resin-based chromatography. Adsorptive membranes with large flow through pores can operate with short residence times but have had low binding capacity. Existing porous hydrogel membranes show improved static binding capacity due to high surface area. However, their small mesh size results in poor macromolecule accessibility, which leads to decreased capacity at short residence times (<60 seconds). High backpressure (>3 bar) due to increased flow rates associated with short residence times is another issue associated with porous hydrogel membranes. Thus, there remains a technological gap for affinity columns with high binding capacity at short residence times. Such an invention would provide an economical increase in downstream biologics purification productivity.

Beyond the need to use long residence times, the small pore structure of conventional resin-based columns further limits its use for larger biologics purification. Particularly, the need for productive purification of large biologics is growing quickly with the advancement of gene & cell therapy industry. Examples of such biologics include plasmid DNA, messenger RNA, virial vectors, virus particles, virus like-particles, and some native and recombinant proteins. These biologics are close to or larger than the pores of resin beads. For these larger biologics, resin-based columns usually have low binding capacity even at long residence times. Resin-based columns are also very easy to clog or foul. Membrane chromatography products with macroporous structure can address the problem. However, no affinity membrane chromatography products are available for such applications.

Accordingly, it is an object of the present invention to provide a membrane and a process for preparing the affinity membrane to rapidly and efficiently purify biologics such as antibodies, plasmid DNA, messenger RNA, viral vectors, virus particles, virus-like particles, native proteins, recombinant proteins, endotoxins and other biologics, in particular, monoclonal antibodies.

It is a further object of the present invention to provide membranes for use in prepacked chromatography columns having short residence times and high binding capacity for antibody capture-step purification under low backpressure.

It is a further object of the present invention to provide a Protein A membrane having a high binding capacity at short residence times and low backpressure.

SUMMARY OF THE INVENTION

The above objectives are accomplished according to the present invention by providing a method for preparing a membrane for binding biologic molecules comprising the steps of immersing a membrane into a first solution of a coupling reagent in a first swelling solvent solution to swell said membrane and increase exposure of reactive sites on said membrane for attachment of said coupling reagent to form coupling groups; immersing said membrane into a second solution comprising adsorptive groups in a second swelling solvent solution to react at least a portion of said coupling groups with adsorptive groups that provide a concentration effect for coupling at least one selected from the group consisting of ligands, nucleotides, oligonucleotides, peptides, polypeptides, proteins, and enzymes to said coupling groups; and, immersing said membrane in an incubating solution selected from the group consisting of ligand, nucleotide, oligonucleotide, peptide, polypeptide, protein, and enzyme solutions having an affinity to a biologic target molecule to couple one of ligands, nucleotides, oligonucleotides, peptides, polypeptides, proteins, and enzymes to at least a portion of said coupling groups of said membrane for binding with said biologic target molecule when exposed to said membrane.

In a further advantageous embodiment, the membrane is a regenerated cellulose membrane with a specific surface area of about 0.1-20 m^2/mL; wherein the ligand is Protein A; wherein said membrane has a dynamic protein binding capacity of between about 20-90 mg human Immunoglobulin G/mL membrane at residence time of about 6 seconds at a backpressure of less than 3 bar; and, wherein said membrane has a static protein binding capacity of greater than 60 mg human Immunoglobulin G/mL membrane.

In a further advantageous embodiment, said first and second swelling solvent solutions comprise at least one swelling solvent selected from the group consisting of dimethyl sulfoxide (DMSO), a mixture of DMSO and other solvents in which the DMSO content is greater than 70% by volume, organic solvents, hexamethylphosphoramide, ionic liquids, sulfolane, and combinations thereof.

In a further advantageous embodiment, said coupling reagent is selected from the group consisting of N,N'-disuccinimidyl carbonate (DSC), 1,1'-carbonyldiimidazole (CDI), N,N'-dicyclohexylcarbodiimide (DCC), 1-ethyl-3-(3-dimethylaminopropyl)carbodiimide hydrochloride) (EDC), Cyanogen halide, Diisocyanates, Diglycidyl ethers, Epichlorohydrin, Tosyl chloride, Glutaraldehyde, Divinyl sulfone, Acyl halides, Triazines, Anhydrides, and combinations thereof.

In a further advantageous embodiment, said adsorptive groups of said second solution are selected from the group consisting of tertiary amine containing groups, functional groups including negatively charged moieties, positively charged moieties, moieties promoting hydrophobic, hydrophilic, and pi-pi stacking interactions, and combinations thereof.

In a further advantageous embodiment, said first and second swelling solvent solutions consist of dimethyl sulfoxide (DMSO), said coupling reagent consists of N,N'-disuccinimidyl carbonate (DSC), said adsorptive groups consists of N,N'-dimethylethylenediamine (DMEDA), said incubating solution comprises a Protein A solution, and said Protein A solution has a Protein A concentration of 10 mg/mL or less.

The above objectives are further accomplished according to the present invention by providing a method for preparing an adsorptive media for binding biologic molecules comprising the steps of providing a macroporous support; immersing said macroporous support in a first solution of a coupling reagent in a solvent solution for attachment of said coupling reagent to form coupling groups; immersing said macroporous support in an incubating solution comprising an organic solvent and a target binding solution selected from the group consisting of ligand, nucleotide, oligonucleotide, peptide, polypeptide, protein, and enzyme solutions having an affinity to a biologic target molecule to couple one of said ligands, nucleotides, oligonucleotides, peptides, polypeptides, proteins, and enzymes to at least a portion of said coupling groups of said macroporous support for binding with said biologic target molecule when exposed to said macroporous support.

In a further advantageous embodiment, said macroporous support is selected from the group consisting of polyolefins membranes, polyethersulfone membranes, poly(tetrafluoroethylene) membranes, nylon membranes, fiberglass membranes, hydrogel membranes, hydrogel monoliths, polyvinyl alcohol membranes; natural polymer membranes, cellulose ester membranes, cellulose acetate membranes, regenerated cellulose membranes, cellulosic nanofiber membranes, cellulosic monoliths, filter paper membranes, and macroporous support membranes containing substantial cellulose or its derivatives, and combinations thereof.

In a further advantageous embodiment, the macroporous support is immersed in a swelling solvent solution to swell said macroporous support and increase exposure of at least one of reactive sites, coupling groups, and ligand sites before or after any step during affinity adsorptive media preparation.

In a further advantageous embodiment, said swelling solvent solution comprises at least one swelling solvent selected from the group consisting of dimethyl sulfoxide (DMSO), a mixture of DMSO and other solvents in which the DMSO content is greater than 70% by volume, organic solvents, hexamethylphosphoramide, ionic liquids, sulfolane, and combinations thereof.

In a further advantageous embodiment, said macroporous support is a regenerated cellulose membrane with a specific surface area of about 0.1-20 m^2/mL; wherein the ligand is Protein A; wherein said macroporous support has a dynamic protein binding capacity of between about 20-90 mg human Immunoglobulin G/mL membrane at residence time of about 6 seconds at a backpressure of less than 3 bar; and, wherein said macroporous support has a static protein binding capacity of greater than 60 mg human Immunoglobulin G/mL membrane.

In a further advantageous embodiment, said coupling reagent is selected from the group consisting of N,N'-disuccinimidyl carbonate (DSC), 1,1'-carbonyldiim idazole (CDI), N,N'-dicyclohexylcarbodiimide (DCC), 1-ethyl-3-(3-dimethylam inopropyl)carbodiimide hydrochloride) (EDC), Cyanogen halides, Diisocyanates, Diglycidyl ethers, Epichlorohydrin, Tosyl chloride, Glutaraldehyde, Divinyl sulfone, Acyl halides, Triazines, Anhydrides, and combinations thereof.

In a further advantageous embodiment, said organic solvent is selected from the group consisting of water-miscible alcohols, ketones, ethers, amides, and combinations thereof, to facilitate coupling one of said ligands, nucleotides, oligonucleotides, peptides, polypeptides, proteins, and enzymes to said macroporous support.

In a further advantageous embodiment, said organic solvent is selected from the group consisting of methanol, ethanol, 1-propanol, 2-propanol, 1-butanol, 2-butanol, acetonitrile, acetone, tetrahydrofuran (THF), dimethylformamide (DMF), and dimethylsulfoxide (DMSO).

In a further advantageous embodiment, said first solution consist of dimethyl sulfoxide (DMSO); said coupling reagent consists of N,N'-disuccinimidyl carbonate (DSC); said incubating solution includes at least one organic solvent selected from the group consisting of methanol, ethanol, 1-propanol, 2-propanol, 1-butanol, 2-butanol, acetonitrile, acetone, tetrahydrofuran (THF), dimethylformamide (DMF), dimethylsulfoxide (DMSO), said incubating solution comprises a Protein A solution; and, said Protein A solution has a Protein A concentration of 10 mg/mL or less.

In a further advantageous embodiment, the amount of said organic solvent in said incubating solution is substantially close to but not significantly greater than the cloud point of the ligand, nucleotide, oligonucleotide, peptide, polypeptide, protein, and enzyme solutions.

The above objectives are further accomplished according to the present invention by providing a method for preparing an adsorptive media for binding biologic molecules comprising the steps of immersing a membrane in a first solution of a coupling reagent selected from the group consisting of N,N'-disuccinimidyl carbonate (DSC), 1,1'-carbonyldiimidazole (CDI), N,N'-dicyclohexylcarbodiimide (DCC), 1-ethyl-3-(3-dimethylaminopropyl)carbodiimide hydrochloride) (EDC), Cyanogen halides, Diisocyanates, Diglycidyl ethers, Epichlorohydrin, Tosyl chloride, Glutaraldehyde, Divinyl sulfone, Acyl halides, Triazines, Anhydrides, and combinations thereof, in a swelling solvent solution to swell said membrane and increase exposure of reactive sites on said membrane for attachment of said coupling reagent to form coupling groups; immersing said membrane in an incubating solution selected from the group consisting of ligand, nucleotide, oligonucleotide, peptide, polypeptide, protein, and enzyme solutions having an affinity to a biologic target molecule to couple one of said ligands, nucleotides, oligonucleotides, peptides, polypeptides, proteins, and enzymes to at least a portion of said coupling groups of said membrane for binding with said biologic target molecule when exposed to said membrane.

In a further advantageous embodiment, said incubating solution includes a kosmotropic salt, selected from the group consisting of sodium phosphate, sodium sulfate, or ammonium sulfate and combinations thereof, to facilitate coupling one of said ligands, nucleotides, oligonucleotides, peptides, polypeptides, proteins, and enzymes to said membrane.

In a further advantageous embodiment, said incubating solution includes an organic solvent, selected from the group consisting of methanol, ethanol, 1-propanol, 2-propanol, 1-butanol, 2-butanol, acetonitrile, acetone, tetrahydrofuran (THF), dimethylformamide (DMF), dimethylsulfoxide (DMSO).

In a further advantageous embodiment, the amount of said organic solvent in said incubating solution is substantially close to but not significantly greater than the cloud point of the ligand, nucleotide, oligonucleotide, peptide, polypeptide, protein, and enzyme solutions.

BRIEF DESCRIPTION OF THE DRAWINGS

The system designed to carry out the invention will hereinafter be described, together with other features thereof. The invention will be more readily understood from a reading of the following specification and by reference to the accompanying drawings forming a part thereof, wherein an example of the invention is shown and wherein.

Figure 1:
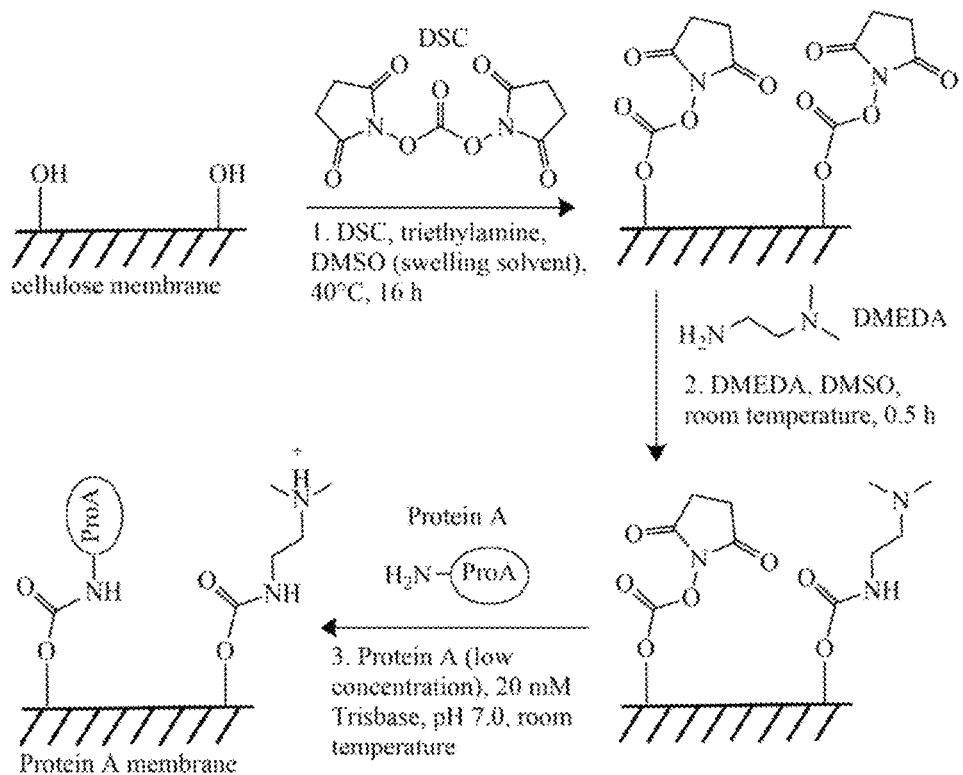
FIG. 1 shows synthesis of Protein A membrane through reaction with DSC, partial substitution with DMEDA, and immobilization of Protein A according to the present invention.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

The present invention comprises an affinity membrane that enables rapid capture step purification of proteins such as monoclonal antibodies (mAbs), plasmid DNA, messenger RNA, viral vectors, virus particles, virus-like particles, native proteins, recombinant proteins, and endotoxins or other target biologics. It offers higher productivity than existing resin products, such as Protein A chromatography columns. In one embodiment of preparing Protein A affinity membrane, the membrane prepared according to the methods described herein is capable of providing a static protein binding capacity of 60-100 mg human Immunoglobulin G/mL, and a dynamic protein binding capacity of 20-90 mg of human Immunoglobulin G/mL at residence time of 6 s or shorter, with <3 bar backpressure.

Protein A columns operate in the bind-and-elute mode. Process productivity can be defined using the equation below. In the denominator, Vtot is the total volume of solution passing through the column during the whole process, including load, rinse, elution, and regeneration steps. BV is the Protein A medium bed volume, and T is residence time. Loading volume is proportional to dynamic binding capacity of the Protein A medium. Thus, process productivity increases with increasing binding capacity and decreasing residence time.

$$\text{Productivity} = \frac{\text{Protein captured}}{\text{Cost of time}} = \frac{\text{Loading volume} \times \text{mAb concentration} \times \text{yield}}{\left(\frac{V_{tot}}{BV}\right) \times \tau}$$

A market leading resin column product operates at a residence time of 360 s, where it has a dynamic binding capacity of 80 mg/mL. For two media with the same dynamic binding capacity that achieve the same product yield, the ratio of load productivities can be estimated by the inverse ratio of residence times. Thus, compared to the membrane of the present invention having 60 mg/mL dynamic binding capacity at 6 seconds residence time, the load productivity of the membrane herein described could be 45 times (=60/80×360 s/6 s) that of a leading resin column product for mAbs capture and purification. There are no resin or membrane products currently available that approach productivity levels achieved by the present invention.

According to the present invention, preparing membranes for use in affinity separation procedures involves different methods of production. In one embodiment, affinity membranes prepared using these methods are differentiated from competing technologies based on their superior binding capacity for proteins such as antibodies, including monoclonal antibodies (mAbs) at short residence times. In example embodiments described herein, the invention involves the use of ligands, nucleotides, oligonucleotides, peptides, polypeptides, proteins, or enzymes, such as oligodeoxythymidine, Protein A, Concanavalin A, trypsin, proteases, or endonucleases, chemically coupled to the membrane; and, in the case of Protein A, offers a static protein binding capacity of 60-100 mg of human Immunoglobulin G/mL and a dynamic protein binding capacity of 20-90 mg of human Immunoglobulin G/mL at residence time of 6 s or shorter, with <3 bar backpressure. In one application, the membranes are used for capture step purification of proteins through bind-and-elute operations.

Membrane Preparation Method 1: This method involves preparing a membrane for binding biologics comprising the steps of 1) immersing the membrane into a first solution composed of a coupling reagent in a swelling solvent to swell said membrane and increase exposure of reactive sites on said membrane for attachment of said coupling reagent; 2) immersing said membrane into a second solution containing adsorptive groups in a second swelling solvent solution to react at least a portion of said coupling groups with adsorptive groups that provide a concentrating effect for coupling at least one of ligands, nucleotides, oligonucleotides, peptides, polypeptides, proteins, and enzymes to said coupling groups; and, 3) immersing said membrane in an incubating solution selected from the group consisting of ligand, nucleotide, oligonucleotide, peptide, polypeptide, protein, and enzyme solutions having an affinity to a biologic target molecule to couple one of said ligands, nucleotides, oligonucleotides, peptides and enzymes to at least a portion of said coupling groups of said membrane for binding with said biologic target molecule when exposed to said membrane. This embodiment of preparing a Protein A affinity membrane is capable of providing a membrane capable of high static protein binding capacities >60 mg human Immunoglobulin G/mL.

Figure 2:
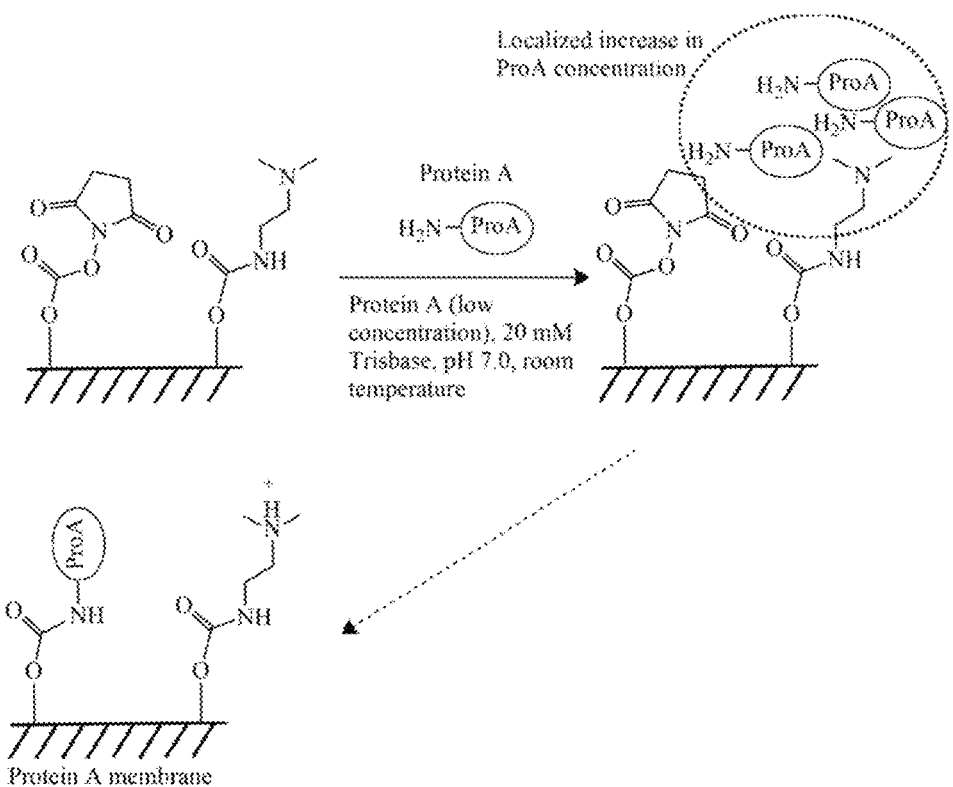
FIG. 2 shows localized concentration of Protein A at the membrane surface and immobilization onto the membrane according to the present invention.

Referring to FIGS. 1 and 2, in one embodiment, the invention includes preparing membranes incorporated with ligands through the concerted use of a solvent that swells the membrane, pre-immobilized coupling, and adsorptive groups. In some embodiments, the membrane is selected from a group including but not limited to materials such as polyolefins, polyethersulfone membranes, poly(tetrafluoroethylene) membranes, nylon membranes, fiberglass membranes, hydrogel membranes, hydrogel monoliths, polyvinyl alcohol membranes; natural polymers, such as cellulose or its derivatives including but not limited to cellulose ester membranes, cellulose acetate membranes, regenerated cellulose membranes, cellulosic nanofiber membranes, cellulosic monolith, or filter papers; or macroporous support containing substantial cellulose or its derivatives. In some embodiments, the swelling solvent is selected from a group including but not limited to chemicals such as organic solvents such as dimethylsulfoxide (DMSO), acetonitrile, tetrahydrofuran (THF), and dimethylformamide (DMF), hexamethylphosphoramide, ionic liquids, sulfolane, or mixtures thereof. In the below detailed embodiment, the membrane comprises regenerated cellulose (RC) and the swelling solvent is DMSO. However, the membrane may be comprised of stabilized regenerated cellulose, or other cellulose based membranes which are incorporated with Protein A ligands as detailed herein, although the method is not limited to this membrane chemistry, as will be appreciated by those skilled in the art.

In one embodiment, membranes with a pore size of between about 0.1 to 10.0 µm, 0.1 µm to 0.2 µm, 0.1 µm to 0.45 µm, 0.1 µm to 1 µm, 0.1 µm to 2 µm, 0.2 to 0.45, 0.2 to 1 µm, 0.2 to 2 µm, 0.2 to 10 µm, 0.45 µm to 1 µm, 0.45 µm to 2 µm, 0.45 µm to 10 µm, 1 µm to 2 µm, or 1 µm to 5 µm, with a thickness of >500 µm, >250 µm, >100 µm, >80 µm, >50 µm, >30 µm, 30 µm to 500 µm, 50 µm to 500 µm, 80 µm to 500 µm, 100 µm to 500 µm, 250 µm to 500 µm, 30 µm to 250 µm, 50 µm to 250 µm, 80 µm to 250 µm, 100 µm to 2500 µm, 30 µm to 100 µm, 50 µm to 100 µm, 80 µm to 100 µm are used. Membranes with a pore size of 1 µm, 0.45 µm, and 0.2 µm were tested and achieved <6 s residence time at <3 bar backpressure, according to the present invention. The membrane can be macroporous or fiber-based. The membranes can be stacked into a multi-layer arrangement to increase capacity for a given application. In one embodiment, the stacked arrangement of membranes is approximately 70 µm to 10,000 µm, >10,000 µm, >7,500 µm, >5,000 µm, >2,500 µm, >1,000 µm, >900 µm, >800 µm, >700 µm, >600 µm, >500 µm, >400 µm, >300 µm, >200 µm, >100 µm, >70 µm, 70 µm to 100 µm, 70 µm to 200 µm, 70 µm to 300 µm, 70 µm to 400 µm, 70 µm to 500 µm, 70 µm to 750 µm, 70 µm to 1,000 µm, 70 µm to 2,000 µm, 70 µm to 3,000 µm, 70 µm to 4,000 µm, 70 µm to 5,000 µm, 250 µm to 300 µm, 250 µm to 400 µm, 250 µm to 500 µm, 250 µm to 750 µm, 250 µm to 1,000 µm, 250 to 2,000 µm, 250 to 3,000 µm, 250 to 4,000 µm, 250 to 5,000 µm, 500 µm to 1,000 µm, 500 to 2,000 µm, 500 to 3,000 µm, 500 to 4,000 µm, 500 to 5,000 µm in thickness. Preferably, the membrane is a regenerated cellulose membrane having a pore size of between 0.2 and 5.0 µm, a thickness of between 70 and 2,000 µm in a stacked arrangement approximately 70 to 10,000 µm high.

Step 1: Membrane Surface Activation in Highly Swollen Solvents:

In a first step of an exemplary embodiment, the regenerated cellulose membranes are soaked in a mixture of N,N'-disuccinimidyl carbonate (DSC), Triethylamine (TEA), and Dimethyl Sulfoxide (DMSO). DMSO is the preferred swelling solvent, other swelling solvents, such as acetonitrile, tetrahydrofuran (THF), and dimethylformamide (DMF) may also be utilized. As shown in FIG. 1, the hydroxyl groups on the regenerated cellulose support membranes reacts with DSC to form amino-reactive carbonate intermediates (—NHS). Membranes prepared using DMSO as the preferred solvent during the surface activation phase have significantly higher binding capacity than membranes prepared using other organic solvents. Swelling solvents increase accessible hydroxyl groups for DSC reaction and hence sites for subsequent protein ligand coupling. In the cases of other solvents for cellulose, less swelling occurs, and surface area and protein ligand coupling sites are lower.

In this exemplary embodiment, the process of the first step can be performed by using from between 0.1-120 mg/mL of DSC, and 5-100 µL/mL of Triethylamine (TEA) in DMSO, acetonitrile, tetrahydrofuran (THF), and dimethylformamide (DMF), hexamethylphosphoramide, sulfolane, or any other solvent/solution that swells the membrane, at a temperature of between about 10-60° C. for between about 1-1,800 minutes. For example, a membrane having a diameter of 47 mm and a thickness of 70 µm is soaked in 300 mg of DSC, 139 µL of TEA, dissolved in 10 mL of DMSO at 40° C. for 16 hours.

Depending on the membrane material, solvents can produce varied amounts of swelling. Accordingly, a solvent that produces a high degree of swelling should be chosen. Regarding cellulose-based membranes, DMSO is a preferred solvent, whether used alone or in combination with other solvents including water. However, other solvents for use with cellulose-based membranes include, but are not limited to other organic solvents such as acetonitrile, tetrahydrofuran (THF), and dimethylformamide (DMF), hexamethylphosphoramide, ionic liquids, sulfolane, or mixtures thereof.

Other than DSC, suitable coupling reagents that may be used include, but are not limited to, 1,1'-carbonyldiimidazole (CDI), N,N'-dicyclohexylcarbodiimide (DCC), 1-ethyl-3-(3-dimethylaminopropyl)carbodiimide hydrochloride) (EDC), Cyanogen halide, Diisocyanates, Diglycidyl ethers, Epichlorohydrin, Tosyl chloride, Glutaraldehyde, Divinyl sulfone, Acyl halides, Triazines, Anhydrides, or mixtures thereof.

Step 2: Modify a Portion of the Activated Surface with Adsorptive Groups:

In one exemplary embodiment, a second step as shown in FIG. 1, the DSC-activated membrane from step 1 is immersed into a solution of N,N-dimethylethylenediamine (DMEDA) in dimethyl sulfoxide (DMSO) solvent to substitute a portion of the coupling groups with a ligand containing tertiary amine groups. DMEDA adsorbs Protein A ligands (See FIG. 2), which assists with the coupling of the Protein A ligands to the membrane in lower concentration solutions.

In this exemplary embodiment, the process of the second step can be performed by using from between about 1-100

μL/mL, <100 μL/mL, <75 μL/mL, <50 μL/mL, <20 μL/mL, <10 μL/mL, 1 to 10 μL/mL, 1 to 20 μL/mL, 1 to 50 μL/mL, 1 to 75 μL/mL, 1 to 100 μL/mL, 10 to 20 μL/mL, 10 to 50 μL/mL, 10 to 75 μL/mL, 10 to 100 μL/mL, 20 to 50 μL/mL, 20 to 75 μL/mL, 20 to 100 μL/mL, 50 to 75 μL/mL, 50 to 100 μL/mL of DMEDA in DMSO, other organic solvents such as acetonitrile, tetrahydrofuran (THF), and dimethylformamide (DMF), hexamethylphosphoramide, sulfolane, or any other solvent/solution that swells the membrane, at between about 10-60° C. for between about 1 minute-24 hours. For example, the membrane is placed in a solution of 15 μL/mL of DMEDA in DMSO at room temperature for 30 minutes.

Other than tertiary amine containing groups, suitable adsorptive groups include functional groups that may include, but are not limited to, negatively charged moieties, positively charged moieties, moieties promoting hydrophobic, hydrophilic, or, pi-pi stacking interactions, or mixtures thereof depending on the ligand that is to be coupled.

Step 3: Ligand Coupling, in One Embodiment, the Ligand is Protein A:

In one exemplary embodiment, a third step as shown in FIG. 1, DMEDA/DSC modified membranes are incubated in Protein A solution. In this step, DMEDA groups are able to enhance protein coupling efficiency through protein physical adsorption. Incorporation of DMEDA groups allows the use of low Protein A concentrations (about 0.5-5 mg/mL) during this step due to the concentrating effects, as shown in FIG. 2. While the illustrated embodiment is described in regards to a Protein A solution, other ligand, nucleotide, oligonucleotide, peptide, polypeptide, protein, or enzyme solutions may be used for a given target which include but are not limited to antibodies, plasmid DNA, messenger RNA, viral vectors, virus particles, virus-like particles, native proteins, recombinant proteins, endotoxins, and other biologics. For example, Protein A solution can be used to target Immunoglobulin G, oligonucleotide solution may be used to target plasmid DNA or messenger RNA, and Concanavalin A solution to target glycoproteins.

In this exemplary embodiment the process of the third step can be performed by using a Protein A concentration of 0.1 to 20 mg/mL, <0.1 mg/mL, <0.5 mg/mL, <0.75 mg/mL, <1 mg/mL, <2.5 mg/mL, <5 mg/mL, <10 mg/mL, <20 mg/mL, <45 mg/mL, 0.1 to 0.5 mg/mL, 0.1 to 0.75 mg/mL, 0.1 to 1 mg/mL, 0.1 to 2.5 mg/mL, 0.1 to 5 mg/mL, 0.1 to 10 mg/mL, 0.1 to 20 mg/mL, 0.1 to 45 mg/mL, 0.5 to 0.75 mg/mL, 0.5 to 1 mg/mL, 0.5 to 2.5 mg/mL, 0.5 to 5 mg/mL, 0.5 to 10 mg/mL, 0.5 to 20 mg/mL, 0.5 to 45 mg/mL, 0.75 to 1 mg/mL, 0.75 to 2.5 mg/mL, 0.75 to 5 mg/mL, 0.75 to 10 mg/mL, 0.75 to 20 mg/mL, 0.75 to 45 mg/mL, 1 to 2.5 mg/mL, 1 to 5 mg/mL, 1 to 10 mg/mL, 1 to 20 mg/mL, 1 to 45 mg/mL, 2.5 to 5 mg/mL, 2.5 to 10 mg/mL, 2.5 to 20 mg/mL, 2.5 to 45 mg/mL, 5 to 10 mg/mL, 5 to 20 mg/mL, 5 to 45 mg/mL, 10 to 20 mg/mL, 10 to 45 mg/mL, 20 to 45 mg/mL, with a buffer of about 0.01-1M Trisbase, phosphate, or carbonate buffer with pH=7.0 at a temperature of between 0-45° C. for any time between about 1 minute and 24 hours. For example, the membrane is placed in a Protein A solution with a Protein A concentration of 5 mg/mL, with 20 mM Trisbase buffer at pH=7.0, at room temperature for 16 hours.

The Protein A ligands coupled to the membrane in the third step of the exemplary embodiment contain sites that can bind antibodies including mAbs. In one embodiment, four layered 70 μm thick membranes prepared using method 1 are stacked in a syringe-filter like column. This arrangement produced a target biologic binding capacity of between about 20-90 mg of human Immunoglobulin G/mL at residence time of ≤6 s and <3 bar backpressure. A widely acknowledged advantage of membrane chromatography is that it does not suffer from the same diffusional mass-transfer limitations that resin or gel chromatography do. The result is that dynamic binding capacities for macroporous adsorptive membranes are less dependent of flow rate over a wide range of residence times. There is a limit at sufficiently short residence times where the characteristic time for protein adsorption is larger than the residence time for flow through the column. However, as long as the target biologic reaction rate is sufficiently fast compared to the convective rate of mass transfer, dynamic capacity will be less affected by residence time.

Membrane Preparation Method 2: This method involves preparing a membrane for binding biologics comprising the steps of 1) immersing the membrane into a solution composed of a coupling reagent in a swelling solvent to swell said membrane and increase exposure of reactive sites on said membrane for attachment of said coupling reagent; and, 2) incubating said membrane in a solution selected from the group consisting of ligands, nucleotides, oligonucleotides, peptides, polypeptides, proteins, and enzymes wherein the solution has a high concentration of the ligands, nucleotides, oligonucleotides, peptides, polypeptides, proteins, and enzymes for coupling to the membrane. In one embodiment of preparing a Protein A affinity membrane, the concentration of Protein A ligand solution is at least 30 mg/mL.

Figure 3:
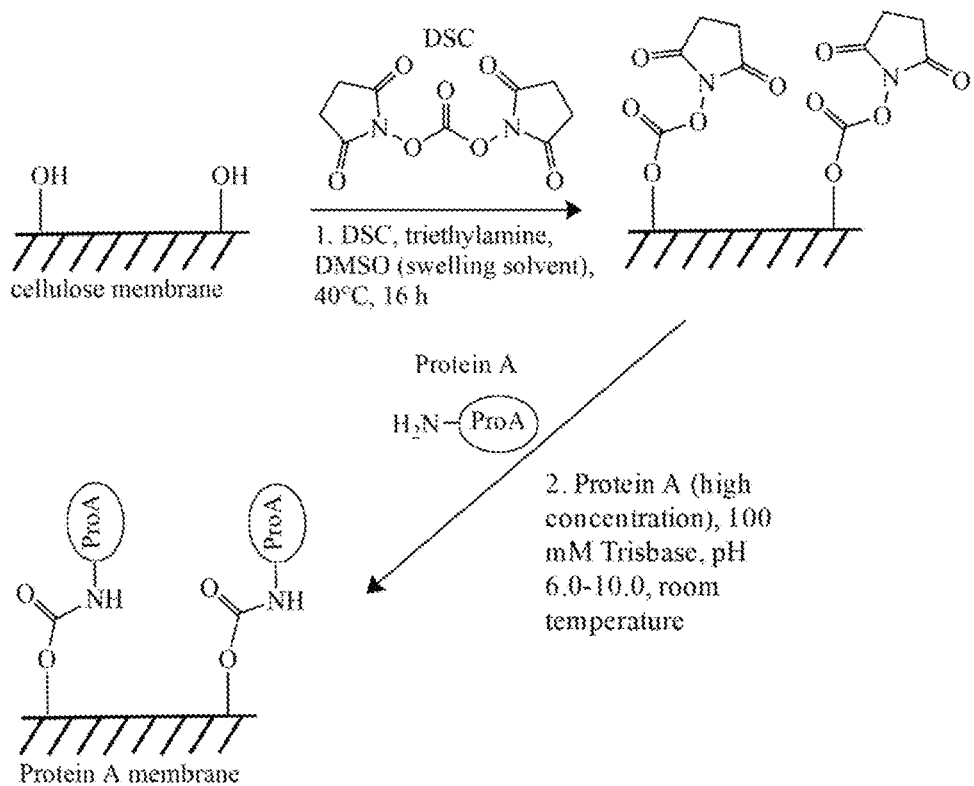
FIG. 3 shows direct modification of a cellulose membrane with DSC followed by immobilization of Protein A at high concentration solution according to the present invention.

While Method 1 allows for high binding capacity using low ligand, nucleotide, oligonucleotide, peptide, polypeptide, protein, or enzyme solution concentrations during coupling to the membrane, Method 2 focuses on high ligand, nucleotide, oligonucleotide, peptide, polypeptide, protein, or enzyme solution concentrations. Referring to FIG. 3, the same high binding capacity with short residence time and low backpressure can also be achieved through direct modification of the membrane, for example, with DSC followed by ligand, nucleotide, oligonucleotide, peptide, polypeptide, protein, and enzyme coupling without the DMEDA adsorptive groups step (Step 2, Method 1 noted above). However, the use of high ligand, oligonucleotides, peptides, polypeptides, proteins, or enzyme solution concentrations (e.g. for Protein A, about >30 mg/mL, >45 mg/mL, >75 mg/mL, >100 mg/mL, 125 mg/mL, >150 mg/mL, >175 mg/mL, 30 to 45 mg/mL, 30 to 100 mg/mL, 30 to 125 mg/mL, 30 to 150 mg/mL, 30 to 200 mg/mL, 45 to 100 mg/mL, 45 to 125 mg/mL, 45 to 150 mg/mL, 45 to 200 mg/mL, 75 to 100 mg/mL, 75 to 125 mg/mL, 75 to 150 mg/mL, 75 to 200 mg/mL, 100 to 125 mg/mL, 100 to 150 mg/mL, 100 to 200 mg/mL, 125 to 150 mg/mL, 125 to 200 mg/mL, 150 to 200 mg/mL) is required. In one embodiment, a Protein A concentration >80 mg/mL is selected.

Figure 8:
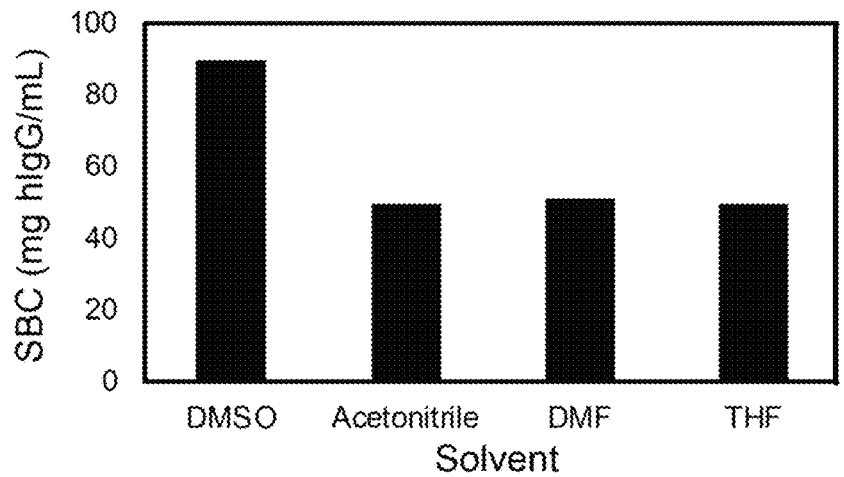
FIG. 8 shows static binding capacity of Protein A membranes prepared using different organic solvents during the surface activation step according to the present invention.

Step 1: Membrane Surface Activation in Highly Swollen Solvents:

In one exemplary embodiment, in a first step, a regenerated cellulose membrane is soaked a mixture of N,N'-disuccinimidyl carbonate (DSC), Triethylamine (TEA), and Dimethyl Sulfoxide (DMSO). DMSO is the preferred swelling solvent, other swelling solvents, such as acetonitrile, tetrahydrofuran (THF), and dimethylformamide (DMF) may also be utilized. As illustrated in FIG. 8, membranes prepared with DMSO, Acetonitrile, DMF, THF as the swelling solvent have static binding capacities of 90, 50, 51, 50 mg human Immunoglobulin G/mL when prepared using Method 2. The hydroxyl groups on the regenerated cellulose support membranes reacts with DSC to form amino-reactive carbonate intermediates (—NHS). Membranes prepared using DMSO as the preferred solvent during the surface activation phase have significantly higher binding capacity than membranes prepared using other organic solvents. Swelling solvents increase accessible hydroxyl groups for DSC reaction and hence sites for subsequent protein ligand coupling. In the cases of other solvents for cellulose, less swelling occurs, and surface area and protein ligand coupling sites are lower.

In one exemplary embodiment, the process of the first step can be performed by using from between 0.1-120 mg/mL of DSC, and 5-100 µL/mL of Triethylamine (TEA) in DMSO, other organic solvents such as acetonitrile, tetrahydrofuran (THF), and dimethylformamide (DMF), hexamethylphosphoramide, sulfolane, or any other solvent/solution that swells the membrane, at a temperature of between about 10-60° C. for between about 1-1,800 minutes. For example, a membrane having a diameter of 47 mm and a thickness of 70 µm is soaked in 300 mg of DSC, 139 µL of TEA, dissolved in 10 mL of DMSO at 40° C. for 16 hours.

Depending on the membrane material, solvents can produce varied amounts of swelling. Accordingly, a solvent that produces a high degree of swelling should be chosen. Regarding cellulose-based membranes, DMSO is a preferred solvent, whether used alone or in combination with other solvents including water. However, other solvents for use with cellulose-based membranes include, but are not limited to, organic solvents such as acetonitrile, tetrahydrofuran (THF), and dimethylformamide (DMF), hexamethylphosphoramide, ionic liquids, sulfolane, or mixtures thereof.

Other than DSC, suitable coupling reagents that may be used include, but are not limited to, 1,1'-carbonyldiimidazole (CDI), N,N'-dicyclohexylcarbodiimide (DCC), 1-ethyl-3-(3-dimethylaminopropyl)carbodiimide hydrochloride) (EDC), Cyanogen halide, Diisocyanates, Diglycidyl ethers, Epichlorohydrin, Tosyl chloride, Glutaraldehyde, Divinyl sulfone, Acyl halides, Triazines, Anhydrides, or mixtures thereof.

Step 2: Ligand Coupling Using High Affinity Ligand Concentration, in One Embodiment, the Ligand is Protein A:

In one exemplary embodiment, in this second step, the DSC modified membranes are directly incubated in Protein A solution, skipping step 2 in Method 1 noted above. However, this requires a high ligand concentration, for example, a Protein A solution concentration >45 mg/mL, as detailed herein.

In one exemplary embodiment, the process of the second step can be performed by using a concentration of about >30 mg/mL, >45 mg/mL, >75 mg/mL, >100 mg/mL, 125 mg/mL, >150 mg/mL, >175 mg/mL, 30 to 45 mg/mL, 30 to 100 mg/mL, 30 to 125 mg/mL, 30 to 150 mg/mL, 30 to 200 mg/mL, 45 to 100 mg/mL, 45 to 125 mg/mL, 45 to 150 mg/mL, 45 to 200 mg/mL, 75 to 100 mg/mL, 75 to 125 mg/mL, 75 to 150 mg/mL, 75 to 200 mg/mL, 100 to 125 mg/mL, 100 to 150 mg/mL, 100 to 200 mg/mL, 125 to 150 mg/mL, 125 to 200 mg/mL, 150 to 200 mg/mL, with a buffer concentration of 0.01-1M Trisbase, phosphate, or carbonate buffer with pH level between about 6.0-10.0, and at a temperature between about 0-45° C. for between about 1 minute and 48 hours. For example, the membrane is placed in a Protein A solution with a Protein A concentration of between about 45-160 mg/mL, with between about 20-200 mM Trisbase buffer at pH=8.0, at room temperature for 16 hours. While the illustrated embodiment is described in regard to a Protein A solution, ligand, nucleotide, oligonucleotide, peptide, polypeptide, protein, or enzyme solutions may be used for a given target which include but are not limited to antibodies, plasmid DNA, messenger RNA, viral vectors, virus particles, virus-like particles, native proteins, recombinant proteins, endotoxins, and other biologics. For example, Protein A solution can be used to target Immunoglobulin G, oligonucleotide solution may be used to target plasmid DNA or messenger RNA, and Concanavalin A solution to target glycoproteins.

Membrane Preparation Method 3: This method involves preparing a membrane for binding biologics comprising the steps of 1) immersing the membrane into a solution composed of a coupling reagent in a swelling solvent to swell said membrane and increase exposure of reactive sites on said membrane for attachment of said coupling reagent; and, 2) incubating said membrane in a solution containing an organic solvent and a target binding solution selected from the group consisting of ligands, oligonucleotides, peptides, polypeptides, proteins, and enzymes to couple one of said ligands, oligonucleotides, peptides, polypeptides, proteins, and enzymes to the membrane. In one embodiment of preparing a Protein A affinity membrane, the concentration of Protein A solution is not greater than 10 mg/mL.

Figure 4:
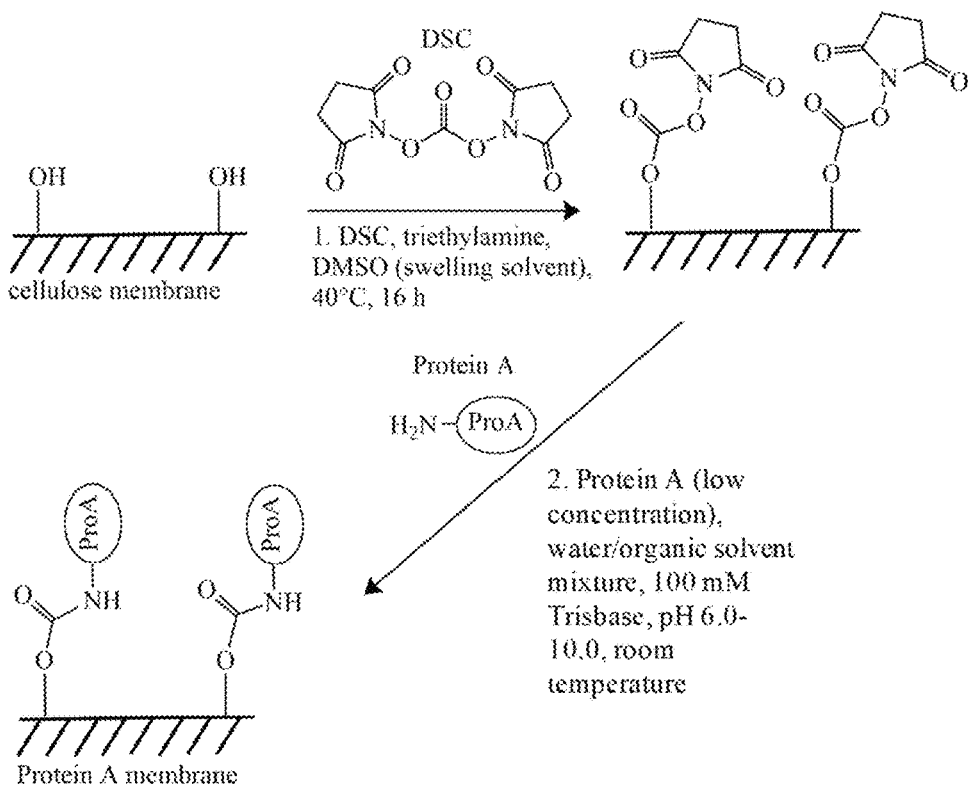
FIG. 4 shows direct modification of a cellulose membrane with DSC followed by immobilization of Protein A at low concentration solution which contains organic solvent according to the present invention.

Method 1 allows for high binding capacity while using low ligand solution concentrations (<5 mg/mL) during ligand coupling. Method 2 allows for high binding capacity but requires high ligand concentration during ligand coupling (Step 2). Referring to FIG. 4, Method 3 utilizes water-miscible organic solvents such as methanol, ethanol, acetone, acetonitrile, tetrahydrofuran (THF), dimethylformamide (DMF), dimethylsulfoxide (DMSO), and any other water-miscible organic solvent such as other alcohols, ketones, ethers, amides, and combinations thereof, as a constituent of the immobilization solution to enhance affinity ligand coupling efficiency, which enables use of low ligand concentrations in the coupling solution. Method 3 utilized increasing proportions of organic solvents (20%-80% by volume, dependent on organic solvent used) to bring solution near the cloud point, which is the point at which the protein solution starts to appear turbid upon increasing the concentration of organic solvent. In Method 3, organic solutions replace water molecules in the protein's solvation shell which can facilitate greater interaction between the ligand and the membrane. Additional organic solutions added beyond cloud point exacerbates aggregation and flocculation dynamics of the ligand, which can comparatively reduce efficiency of coupling reaction.

Step 1: Membrane Surface Activation in Highly Swollen Solvents:

In an exemplary embodiment, in a first step, a regenerated cellulose membrane is soaked in a mixture of N,N'-disuccinimidyl carbonate (DSC), Triethylamine (TEA), and Dimethyl Sulfoxide (DMSO). DMSO is the preferred swelling solvent, other swelling solvents, such as acetonitrile, tetrahydrofuran (THF), and dimethylformamide (DMF) may also be utilized. The hydroxyl groups on the regenerated cellulose support membranes reacts with DSC to form amino-reactive carbonate intermediates (—NHS). Membranes prepared using DMSO as the preferred solvent during the surface activation phase have significantly higher binding capacity than membranes prepared using other organic solvents. Swelling solvents increase accessible hydroxyl groups for DSC reaction and hence sites for subsequent protein ligand coupling. In the cases of other solvents for cellulose, less swelling occurs, and surface area and protein ligand coupling sites are lower.

In this exemplary embodiment, the process of the first step can be performed by using from between 0.1-120 mg/mL of DSC, and 5-100 µL/mL of Triethylamine (TEA) in DMSO, other organic solvents such as acetonitrile, tetrahydrofuran (THF), and dimethylformamide (DMF), hexamethylphosphoramide, sulfolane, or any other solvent/solution that swells the membrane, at a temperature of between about 10-60° C. for between about 1-1,800 minutes. For example, a membrane having a diameter of 47 mm and a thickness of 70 µm is soaked in 300 mg of DSC, 139 µL of TEA, dissolved in 10 mL of DMSO at 40° C. for 16 hours.

Depending on the membrane material, solvents can produce varied amounts of swelling. Accordingly, a solvent that produces a high degree of swelling should be chosen. Regarding cellulose-based membranes, DMSO is a preferred solvent, whether used alone or in combination with other solvents including water. However, other solvents for use with cellulose-based membranes include, but are not limited to, other organic solvents such as acetonitrile, tetrahydrofuran (THF), and dimethylformamide (DMF), hexamethylphosphoramide, ionic liquids, sulfolane, or mixtures thereof.

Other than DSC, suitable coupling reagents that may be used include, but are not limited to, 1,1'-carbonyldiimidazole (CDI), N,N'-dicyclohexylcarbodiimide (DCC), 1-ethyl-3-(3-dimethylaminopropyl)carbodiimide hydrochloride) (EDC), Cyanogen halide, Diisocyanates, Diglycidyl ethers, Epichlorohydrin, Tosyl chloride, Glutaraldehyde, Divinyl sulfone, Acyl halides, Triazines, Anhydrides, or mixtures thereof.

Step 2: Ligand Coupling Using Low Ligand Concentration, in One Embodiment, the Ligand is Protein A:

In one exemplary embodiment, in this second step, the DSC, Tosyl chloride, or Epichlorohydrin, modified membranes are directly incubated in low concentration of Protein A solution containing organic solvents including methanol, ethanol, 1-propanol, 2-propanol, 1-butanol, 2-butanol, acetonitrile, acetone.

In one exemplary embodiment, the process of the second step can be performed by using an affinity ligand concentration of about 0.1 to 20 mg/mL, <0.1 mg/mL, <0.5 mg/mL, <0.75 mg/mL, <1 mg/mL, <2.5 mg/mL, <5 mg/mL, <10 mg/mL, <20 mg/mL, <45 mg/mL, 0.1 to 0.5 mg/mL, 0.1 to 0.75 mg/mL, 0.1 to 1 mg/mL, 0.1 to 2.5 mg/mL, 0.1 to 5 mg/mL, 0.1 to 10 mg/mL, 0.1 to 20 mg/mL, 0.1 to 45 mg/mL, 0.5 to 0.75 mg/mL, 0.5 to 1 mg/mL, 0.5 to 2.5 mg/mL, 0.5 to 5 mg/mL, 0.5 to 10 mg/mL, 0.5 to 20 mg/mL, 0.5 to 45 mg/mL, 0.75 to 1 mg/mL, 0.75 to 2.5 mg/mL, 0.75 to 5 mg/mL, 0.75 to 10 mg/mL, 0.75 to 20 mg/mL, 0.75 to 45 mg/mL, 1 to 2.5 mg/mL, 1 to 5 mg/mL, 1 to 10 mg/mL, 1 to 20 mg/mL, 1 to 45 mg/mL, 2.5 to 5 mg/mL, 2.5 to 10 mg/mL, 2.5 to 20 mg/mL, 2.5 to 45 mg/mL, 5 to 10 mg/mL, 5 to 20 mg/mL, 5 to 45 mg/mL, 10 to 20 mg/mL, 10 to 45 mg/mL, 20 to 45 mg/mL, with a buffer concentration of 0.01-1M Trisbase, phosphate, or carbonate buffer mixed with a significant portion of organic solvents, with pH level between about 6.0-10.0, and at a temperature between about 0-45° C. for between about 1 minute and 48 hours. For example, the membrane is placed in a Protein A solution with a Protein A concentration of between about 0.1-20 mg/mL, with between about 20-200 mM Trisbase buffer at pH=8.0, at room temperature for 16 hours. However, greater concentrations of Protein A can be used (20 to 175 mg/mL). The organic solvent fraction is 1%-99% by volume, whatever is required to bring solution near cloud point, which is the point at which the protein solution starts to appear turbid upon increasing the concentration of organic solvent. Organic solvents suitable for use in the present invention include, but are not limited to methanol, ethanol, 1-propanol, 2-propanol, 1-butanol, 2-butanol, acetonitrile, acetone, tetrahydrofuran (THF), and dimethylformamide (DMF).

It can be appreciated by one skilled in the art that optimal proportions are ligand and organic solvent dependent. Furthermore, there is additional advantage of this methodology when using water-labile linkers, since the addition of organic solvent reduces the rate of hydrolysis relative to rate of the amine coupling reaction, improving coupling efficiency. While the illustrated embodiment is described in regard to a Protein A solution, other ligand, nucleotide, oligonucleotide, peptide, polypeptide, protein, or enzyme solutions, may be used for a given target which include but are not limited to antibodies, plasmid DNA, messenger RNA, viral vectors, virus particles, virus-like particles, native proteins, recombinant proteins, endotoxins, and other biologics. For example, Protein A solution can be used to target Immunoglobulin G, oligonucleotide solution may be used to target plasmid DNA or messenger RNA, Concanavalin A solution to target glycoproteins.

The amount of organic solvent in the incubating solution should be substantially close to but not significantly greater than the cloud point. It is possible to define a range of appropriate amounts of organic solvent in the incubating solution in which the upper boundary is expressed by $[V\%_{cp}+a(100\%-V\%_{cp})]$ and the lower boundary is expressed by $[V\%_{cp}-bV\%_{cp}]$, where "$V\%_{cp}$" is the percent by volume of the organic solvent in the ligand solution at the cloud point, "a" is the upper deviation from the cloud point, and "b" is the lower deviation from the cloud point. For the purpose of an example, if the percent by volume of the organic solvent in the ligand solution at the cloud point ($V\%_{cp}$) is 60%, and the upper and lower boundaries are defined by a=0.3 and b=0.5, then the corresponding appropriate amounts of organic solvent in the incubating solution would range from 30% to 72% organic solvent by volume. In one exemplary embodiment, the process of the second step can be performed by using an amount of organic solvent in the incubating solution in which "a" is about 0.01, 0.02, 0.03, 0.04, 0.05, 0.06, 0.07, 0.08, 0.09, 0.1, 0.12, 0.14, 0.16, 0.18, 0.2, 0.25, 0.3, 0.4, 0.5, 0.6, 0.7, 0.8, 0.9, 0.99 and "b" is about 0.01, 0.02, 0.03, 0.04, 0.05, 0.06, 0.07, 0.08, 0.09, 0.1, 0.12, 0.14, 0.16, 0.18, 0.2, 0.25, 0.3, 0.4, 0.5, 0.6, 0.7, 0.8, 0.9, 0.99. In the case of 5 mg/mL Protein A in 100 mM Tris, the volumetric percentage for methanol, ethanol, 1-propanol, 2-propanol, 1-butanol, 2-butanol, acetonitrile, acetone to bring solution just below cloud point were found to be approximately 74%, 62%, 50%, 57%, 20%, 20%, 43%, 50% respectively. While the illustrated embodiment is described in regard to a Protein A solution, other ligand, nucleotide, oligonucleotide, peptide, polypeptide, protein, or enzyme solutions, may be used for a given target which include but are not limited to antibodies, plasmid DNA, messenger RNA, viral vectors, virus particles, virus-like particles, native proteins, recombinant proteins, endotoxins, and other biologics. For example, Protein A solution can be used to target Immunoglobulin G, oligonucleotide solution may be used to target plasm id DNA or messenger RNA, Concanavalin A solution to target glycoproteins.

Figure 5:
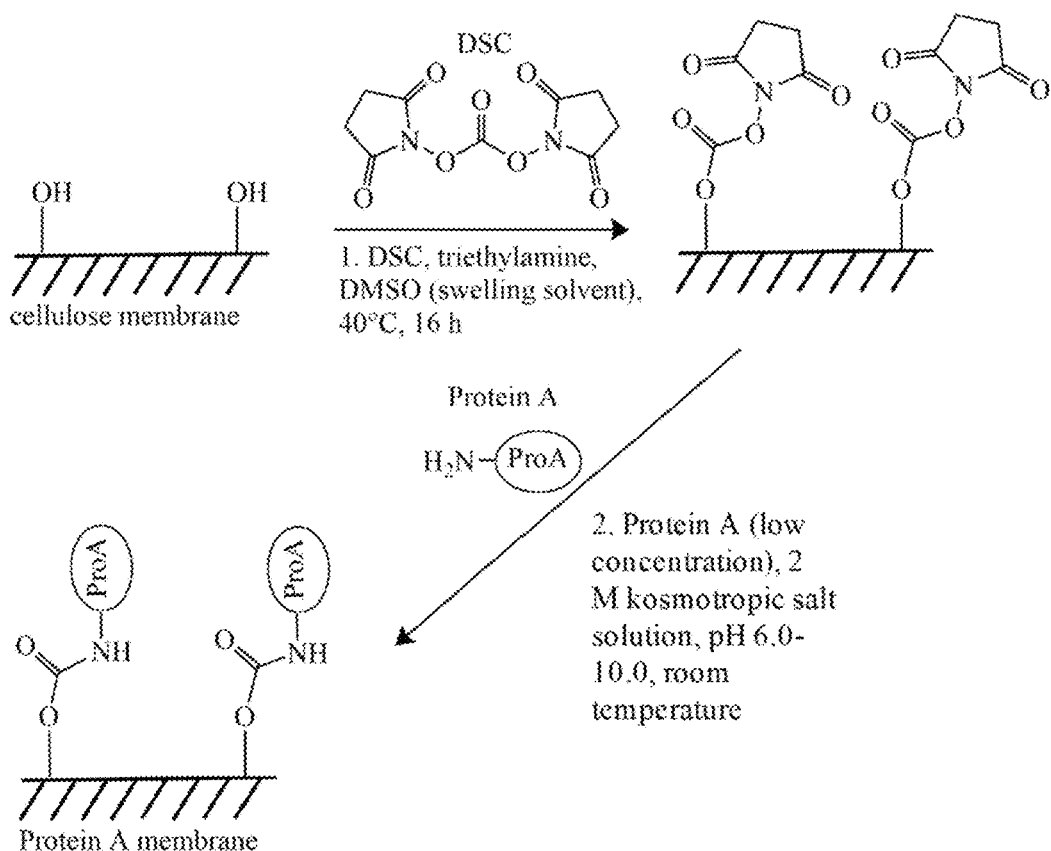
FIG. 5 shows direct modification of a cellulose membrane with DSC followed by immobilization of Protein A at low concentration solution which contains kosmotropic salts according to the present invention.

Membrane Preparation Method 4: This method is similar to Method 3 but involves the use of kosmotropic salt instead of an organic solvent. Method 1 allows for high binding capacity while using low ligand solution concentrations during ligand coupling. Method 2 allows for high binding capacity but requires high ligand concentration during ligand coupling (Step 2). Method 3 utilizes water-miscible organic solvents as a constituent of the immobilization solution to enhance ligand coupling efficiency, which enables use of low ligand, nucleotide, oligonucleotide, peptide, polypeptide, protein, and enzyme concentrations in the coupling solution. Referring to FIG. 5, under Method 4, this high capacity could also be achieved through direct modification of the membrane with DSC followed by Protein A ligand coupling with the utilization of kosmotropic salts including, but not limited to, sodium phosphate, sodium sulfate, or ammonium sulfate.

Method 4 utilizes increasing proportions of kosmotropic salts to bring the ligand solution substantially close to but not significantly greater than the cloud point, which is the point at which the protein solution starts to appear turbid upon increasing the concentration of kosmotropic salt, additional salt added beyond this point can exacerbate aggregation and flocculation dynamics of the ligand, which can comparatively reduce efficiency of coupling reaction. In Method 4, kosmotropic salts disrupt the protein's solvation shell which can facilitate greater interaction between Protein A and the membrane. Near the cloud point, repulsive electrostatic interactions between ligand molecules are mitigated by compression of the solvation layer and interactions between charged groups in the protein and the salt enforcing interaction between the now more-exposed hydrophobic portions of the protein and the membrane, increasing localization of ligand along the membrane/solution interface, which can enhance efficiency of the coupling reaction.

Step 1: Membrane Surface Activation in Highly Swollen Solvents:

In an exemplary embodiment, in a first step, a regenerated cellulose membrane is soaked in N,N'-disuccinimidyl carbonate (DSC), Triethylamine (TEA), and Dimethyl Sulfoxide (DMSO). DMSO swells cellulose more significantly compared to many other organic solvents, such as acetonitrile, tetrahydrofuran (THF), and dimethylformamide (DMF). The hydroxyl groups on the regenerated cellulose support membranes reacts with DSC to form amino-reactive carbonate intermediates (—NHS). Membranes prepared using DMSO as the preferred solvent during the surface activation phase have significantly higher binding capacity than membranes prepared using other organic solvents. Swelling solvents increase accessible hydroxyl groups for DSC reaction and hence sites for subsequent protein ligand coupling. In the cases of other solvents for cellulose, less swelling occurs, and surface area and protein ligand coupling sites are lower.

In this exemplary embodiment, the process of the first step can be performed by using from between 0.1-120 mg/mL of DSC, and 5-10 μL/mL of Triethylamine (TEA) in DMSO, other organic solvents, such as acetonitrile, tetrahydrofuran (THF), and dimethylformamide (DMF), hexamethylphosphoramide, sulfolane, or any other solvent/solution that swells the membrane, at a temperature of between about 10-60° C. for between about 1-1,800 minutes. For example, a membrane having a diameter of 47 mm and a thickness of 70 μm is soaked in 300 mg of DSC, 139 μL of TEA, dissolved in 10 mL of DMSO at 40° C. for 16 hours.

Depending on the membrane material, solvents can produce varied amounts of swelling. Accordingly, a solvent that produces a high degree of swelling should be chosen. Regarding cellulose-based membranes, DMSO is a preferred solvent, whether used alone or in combination with other solvents including water. However, other solvents for use with cellulose-based membranes include, but are not limited to, other organic solvents such as acetonitrile, tetrahydrofuran (THF), and dimethylformamide (DMF), hexamethylphosphoramide, ionic liquids, sulfolane, or mixtures thereof.

Other than DSC, suitable coupling reagents that may be used include, but are not limited to, 1,1'-carbonyldiimidazole (CDI), N,N'-dicyclohexylcarbodiimide (DCC), 1-ethyl-3-(3-dimethylaminopropyl)carbodiimide hydrochloride) (EDC), Cyanogen halide, Diisocyanates, Diglycidyl ethers, Epichlorohydrin, Tosyl chloride, Glutaraldehyde, Divinyl sulfone, Acyl halides, Triazines, Anhydrides, or mixtures thereof.

Step 2: Ligand Coupling Using Low Affinity Ligand Concentration, in One Embodiment, the Ligand is Protein A:

In one exemplary embodiment, in this second step, the DSC modified membranes are directly incubated in low concentration of Protein A solution in concentrated kosmotropic salt solution.

In one exemplary embodiment, the process of the second step can be performed by using a concentration of ligand about 1 to 20 mg/mL, <1 mg/mL, <2.5 mg/mL, <5 mg/mL, <10 mg/mL, <20 mg/mL, <45 mg/mL, 1 to 2.5 mg/mL, 1 to 5 mg/mL, 1 to 10 mg/mL, 1 to 20 mg/mL, 1 to 45 mg/mL, 2.5 to 5 mg/mL, 2.5 to 10 mg/mL, 2.5 to 20 mg/mL, 2.5 to 45 mg/mL, 5 to 10 mg/mL, 5 to 20 mg/mL, 5 to 45 mg/mL, 10 to 20 mg/mL, 10 to 45 mg/mL, 20 to 45 mg/mL, with a salt concentration of 0.5-3 M, 0.5 to 1 M, 0.5 to 2 M, 0.5 to 2.5 M, 0.5 to 3 M, 1 to 2 M, 1 to 2.5 M, 1 to 3 M, 1.5 to 2 M, 1.5 to 2.5 M, 1.5 to 3 M, 2 to 2.5 M, 2 to 3 M, 2.5 to 3 M, with pH level between about 6.0-10.0, and at a temperature between about 0-45° C. for between about 1 minute and 48 hours. For example, the membrane is placed in a Protein A solution with a Protein A concentration of between about 5 mg/mL, with about 2 M $Na_2SO_4$ at pH=6.5, at room temperature for 16 hours. However, greater concentrations of Protein A can be used (20 to 175 mg/mL). The kosmotropic salt concentration can be between 0.5 and 3M to bring solution near but preferably under the cloud point (as detailed above in Method 3), which is the point at which the protein solution starts to appear turbid upon increasing the concentration of kosmotropic salt. It can be appreciated by one skilled in the art that optimal proportions are ligand and kosmotropic salt dependent. While the illustrated embodiment is described in regard to a Protein A solution, other ligand, nucleotide, oligonucleotide, peptide, polypeptide, protein, or enzyme solutions, may be used for a given target which include but are not limited to antibodies, plasmid DNA, messenger RNA, viral vectors, virus particles, virus-like particles, native proteins, recombinant proteins, endotoxins, and other biologics. For example, Protein A solution can be used to target Immunoglobulin G, oligonucleotide solution may be used to target plasmid DNA or messenger RNA, Concanavalin A solution to target glycoproteins.

Membrane Preparation Method 5: This method involves preparing a membrane for binding biologics by using a swelling solvent before or after any step during affinity membrane preparation as described in Methods 1-4. In one embodiment, the swelling solvent is DMSO and the ligand is Protein A and a regenerated cellulose membrane was presoaked in DMSO before an activation step followed by Protein A ligand immobilization. In another embodiment, a regenerated cellulose membrane was soaked in DMSO after an activation step followed by Protein A ligand immobilization. In another embodiment, a Protein A functionalized regenerated cellulose membrane was soaked in DMSO. The results indicated that the swelling can improve binding capacity by 45% over unswollen membranes in these various arrangements.

In one embodiment, regenerated cellulose membrane was presoaked in DMSO before an activation step followed by Protein A ligand immobilization. For example, a membrane having a diameter of 47 mm and a thickness of 70 μm is soaked in 10 mL of DMSO at 40° C. for 16 hours.

In another embodiment, regenerated cellulose membrane was soaked in DMSO after an activation step followed by Protein A ligand immobilization. For example, an NHS-activated membrane having a diameter of 47 mm and a thickness of 70 μm is soaked in 10 mL of DMSO at 40° C. for 16 hours.

In another embodiment, a Protein A functionalized regenerated cellulose membrane was soaked in DMSO. For example, a Protein A functionalized membrane having a diameter of 47 mm and a thickness of 70 μm is soaked in 10 mL of DMSO at 40° C. for 16 hours.

In Method 5, it is not necessary to have the activation step completed in a swelling solvent as a swelling step before or after any step can increase the exposure of reactive sites, coupling sites, or ligand sites in a manner sufficient to yield a membrane with high binding capacity.

Membrane Performance:

Key performance measures of columns with membranes prepared according to the above noted methods include static binding capacity (SBC) and dynamic binding capacity at 10% breakthrough ($DBC_{10\%}$). In one embodiment, the principal biologic studied during testing was purified polyclonal human Immunoglobulin G (hIgG), since it is used often in the industry as a model antibody for standardizing performance testing of Protein A based products. These proteins are antibodies with molecular weight of approximately 150,000 Da. Isoelectric points of these molecules were not specifically determined during testing, but they range from 6.1 to 9.4.

Figure 6:
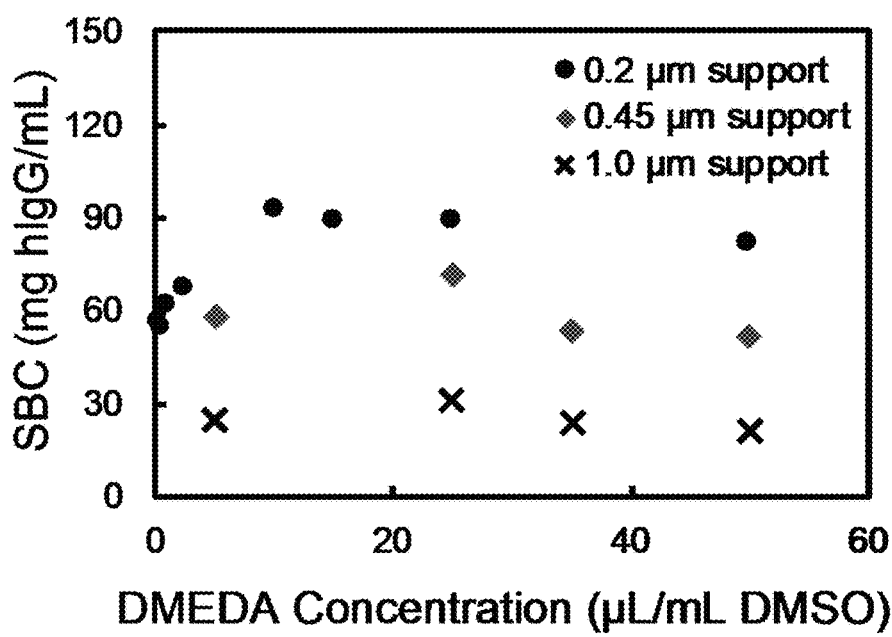
FIG. 6 shows static binding capacity of Protein A membranes prepared using Method 1 according to the present invention.

In another embodiment, Concanavalin A (Con A) was used as affinity ligand. Con A has been used to purify glycosylated proteins. To evaluate the performance of Con A affinity membranes, hIgG or porcine thyroglobulin were used, which are industry standards.

i: SBC measurements: Static binding capacity (SBC) tests provide a good benchmark for initial screening studies. SBCs were measured by mass balance using initial and equilibrium hIgG concentrations measured using a Nanodrop UV Spectrophotometer. FIG. 6 shows that SBC of Protein A membranes prepared by Method 1 changes with the concentration of DMEDA in Step 2 (Method 1). The Protein A concentration used in this study was 5 mg/mL in 20 mM Tris with pH 7.0. hIgG was used as model antibody. DMSO is used as the solvent in all of examples noted. The highest SBC yielded using Method 1 is greater than 100 mg/mL.

Figure 7:
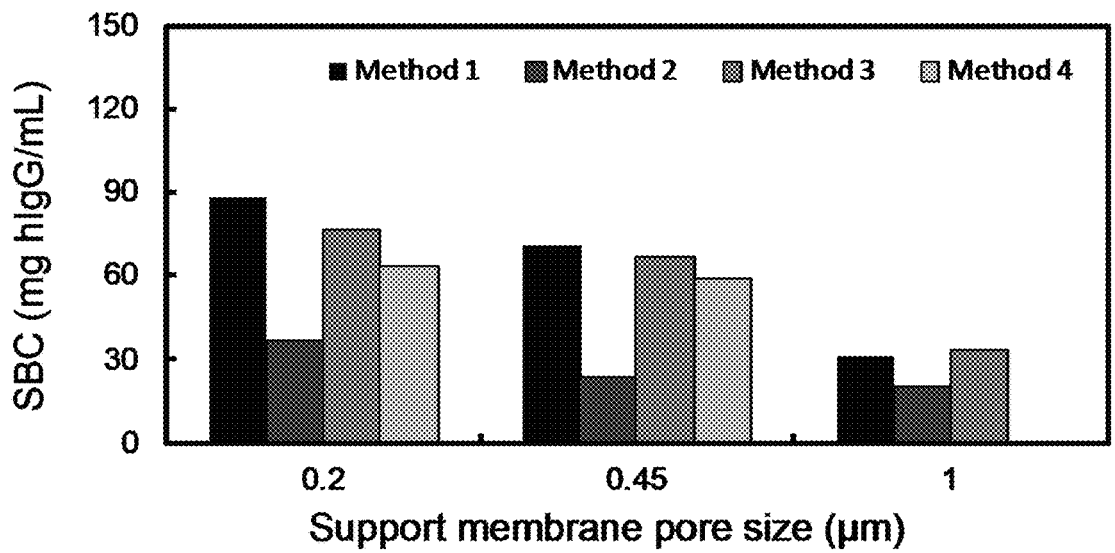
FIG. 7 shows static binding capacity comparison of Protein A membranes prepared using Methods 1-4 according to the present invention.

FIG. 7 compares the SBC of Protein A membranes with 1, 0.45 and 0.2 μm pore sizes prepared using Methods 1, 2, 3 and 4. In this example, 5 mg/mL Protein A solution was used during ligand coupling for Methods 1, 2 and 3. Method 4 uses 16.6 mg/mL Protein A solution. Overall, Methods 1, 3, and 4 yield much higher SBC than Method 2 using a lower concentration Protein A solution. The SBC performance difference is more significant for smaller pore size support membranes. Accordingly, Method 2 requires greater than 45 mg/mL Protein A concentration to achieve similar results to Methods 1, 3 and 4. Data was not collected for 1 μm pore size membranes using Method 4.

Figure 9:
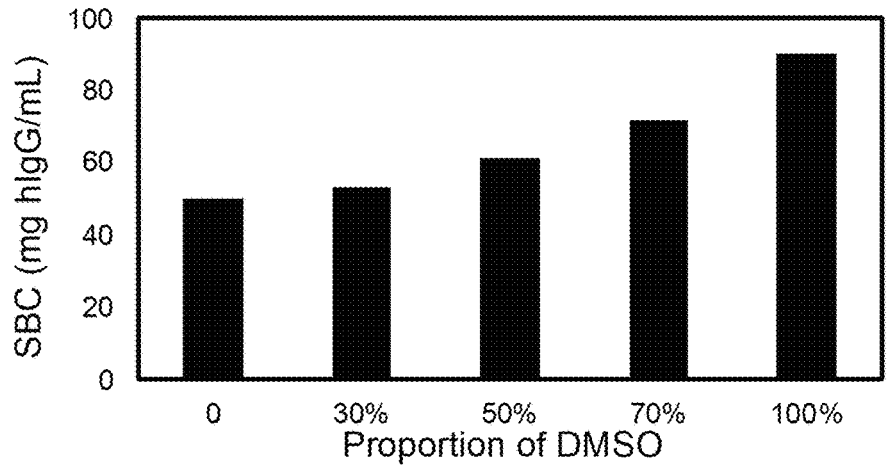
FIG. 9 shows static binding capacity of Protein A membranes prepared with DMSO/Acetonitrile mixed solvents during the surface activation step using Method 2 according to the present invention.
Figure 10:
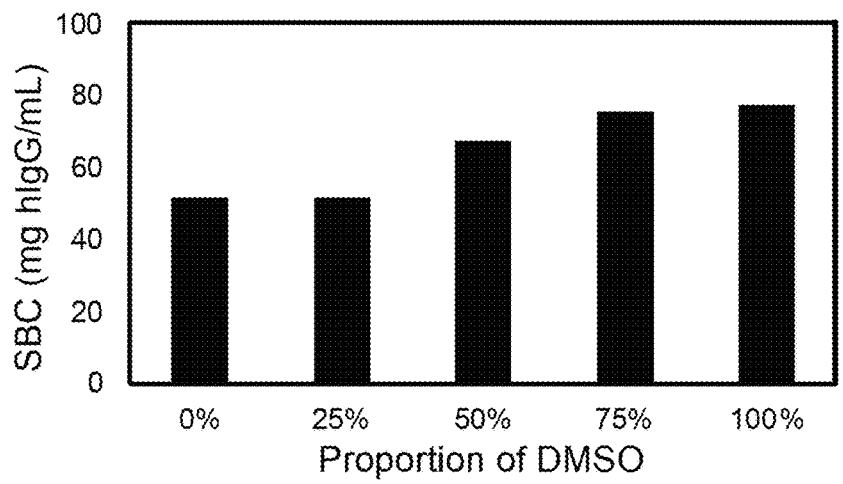
FIG. 10 shows static binding capacity of Protein A membranes prepared with DMSO/Acetonitrile mixed solvents during the surface activation step using Method 3 according to the present invention.

FIG. 8 shows that membrane prepared using DMSO as the swelling solvent during surface activation has significantly higher hIgG binding capacity than membranes prepared using acetonitrile, DMF, or THF using Method 2. This was prepared using 90 mg/mL Protein A in 100 mM of trisbase at pH 8.0-9.0. In FIG. 9, it shows that IgG binding capacity of membranes activated with different volume proportions of DMSO-acetonitrile mixed solvents (0, 30%, 50%, 70%, 100% DMSO) using Method 2 using 90 mg/mL Protein A in 100 mM of trisbase at pH 8.0-9.0. The membrane binding capacity increases with DMSO content as swelling solvents increase accessible hydroxyl groups for DSC reaction and hence sites for subsequent protein ligand coupling. The same trend has also been observed using Method 3 to prepare Protein A affinity membrane adsorbers, as is shown in FIG. 10, which was prepared using DMSO-acetonitrile mixed solvents during Step 1 (Method 3) and 5 mg/mL Protein A in 100 mM of trisbase at pH 8.0-9.0 with ~60% ethanol by volume during the ligand coupling step.

Figure 11:
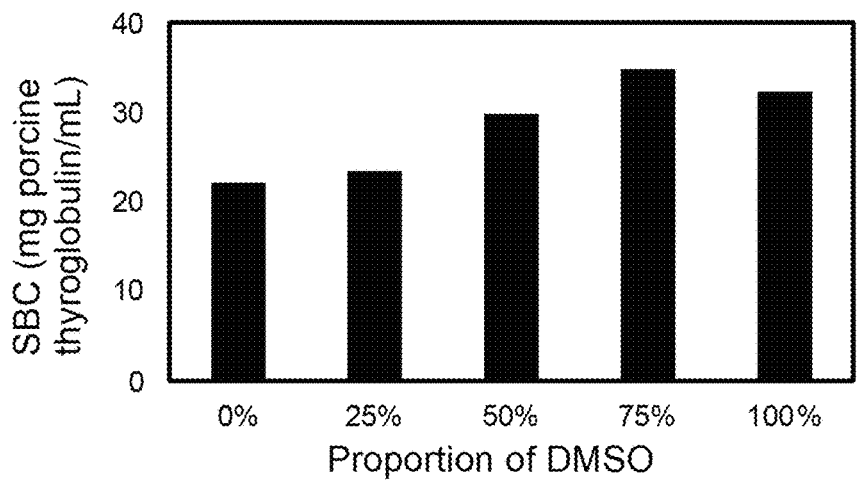
FIG. 11 shows static binding capacity of Concanavalin A membranes prepared with DMSO/Acetonitrile mixed solvents during the surface activation step using Method 3 according to the present invention.

In FIG. 11, Con A membranes were prepared by Method 3, using different volume proportion of DMSO-acetonitrile (0, 25%, 50%, 75%, 100% DMSO) in the membrane activation step. Ethanol (19.6% by volume) was used as the organic solvent in the ligand coupling step, and concentration of Con A ligand was 5 mg/ml. Porcine thyroglobulin was used as the probe protein to measure SBC in 20 mM Tris pH 7.4, 0.5 M NaCl, 1 mM $MnCl_2$, 1 mM $CaCl_2$. The binding capacity generally also increases with DMSO volume proportion used.

Table 1 shows that SBC of Protein A membranes activated with DMSO/Acetonitrile mixed solvents followed by Protein A immobilization in different buffer conditions. Overall, SBC decreases as solvent used in the activation step transitions from DMSO to acetonitrile, as swelling solvents increase accessible hydroxyl groups for DSC reaction and hence sites for subsequent protein ligand coupling.

TABLE 1

SBC of membranes prepared with DMSO-Acetonitrile mixed solvents during step 1 using Method 3 with ~60% ethanol by volume using 100 mM of given buffer at given pH and 5 mg/mL Protein A during the ligand coupling step.

| | SBC | | | | | |
|---|---|---|---|---|---|---|
| | Carbonate pH 8 | Carbonate pH 9 | Phosphate ph 8 | Phosphate pH 9 | Tris pH 8 | Tris pH 9 |
| DMSO | 72.7 | 63.8 | 58.9 | 68.3 | 77.3 | 73.4 |
| DMSO 75%-25% Acetonitrile | 69.8 | 65.2 | 65.5 | 62.0 | 75.4 | 72.9 |
| DMSO 50%-50% Acetonitrile | 67.6 | 56.4 | 61.6 | 55.2 | 67.5 | 67.8 |
| DMSO 25%-75% Acetonitrile | 47.4 | 40.7 | 47.2 | 39.0 | 51.8 | 52.1 |
| Acetonitrile | 42.6 | 38.4 | 38.2 | 36.2 | 51.5 | 51.2 |

Figure 12:
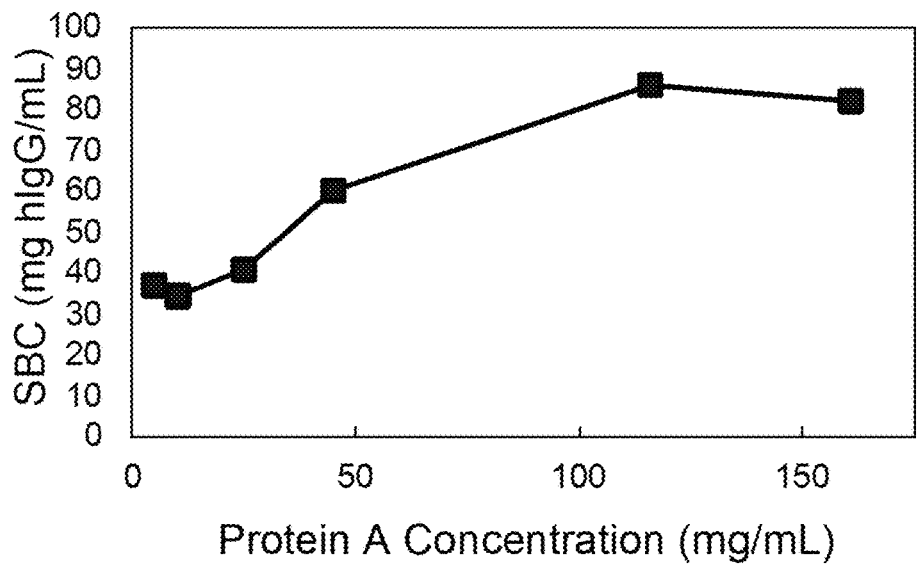
FIG. 12 shows static binding capacity changes with increased Protein A concentration using Method 2 according to the present invention.

FIG. 12 shows the need to use a Protein A concentration >100 mg/mL in the ligand coupling step of Method 2 to achieve SBC >80 mg hIgG/mL. By comparison, in Methods 1, 3 and 4, one can use concentration <20 mg/mL Protein A solution to prepare SBC membranes >80 mg hIgG/mL. As a result, Methods 1, 3 and 4 can significantly reduce membrane production cost as a reduced protein concentration is sufficient to produce membranes with equivalent binding capacity.

Figure 13:
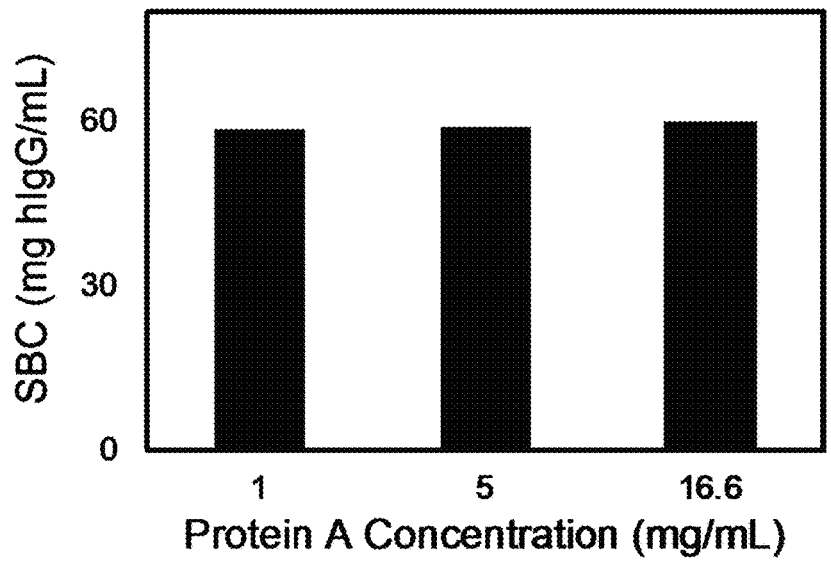
FIG. 13 shows static binding capacity changes with 1-16.6 mg/mL Protein A concentration using Method 4 according to the present invention.

In FIG. 13, the membranes were prepared by Method 4. The figure shows the SBC remains similar across the range of Protein A concentrations in coupling solution with 2 M of sodium sulfate. The 0.2 um pore size support membranes were soaked in 5 mg DSC/mL DMSO during the activation step.

Figure 14:
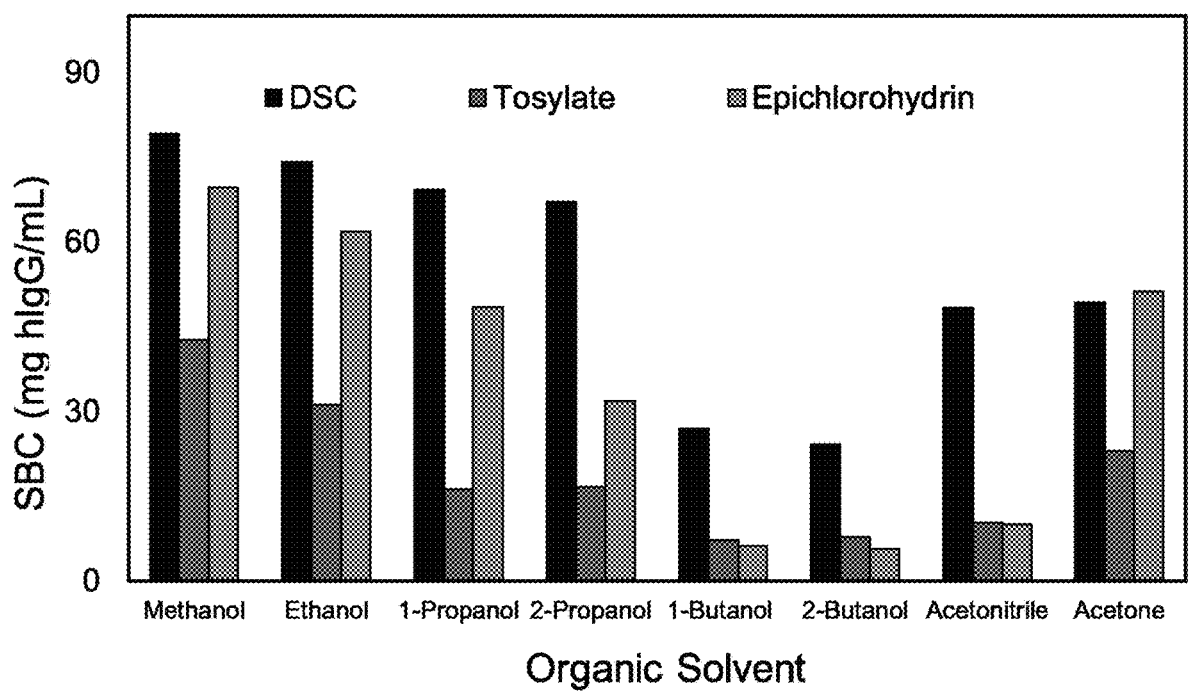
FIG. 14 shows static binding capacity of Protein A membranes prepared using different coupling reagents and organic solvents using Method 3 according to the present invention.

FIG. 14 shows that high capacity Protein A membranes can be obtained with a variety of coupling reagents using Method 3. In this example, DSC, Tosyl Chloride, and Epichlorohydrin were used to activate regenerated cellulose membranes with pore sizes of 0.2 μm. These membranes were soaked in the following solutions respectively: A solution containing 5 mg DSC/mL DMSO; a solution containing 0.12 mL 1 M NaOH, 0.13 mL Epichlorohydrin/mL DMSO; and a solution containing 22.5 mg Tosyl chloride/mL DMSO.

Figure 15:
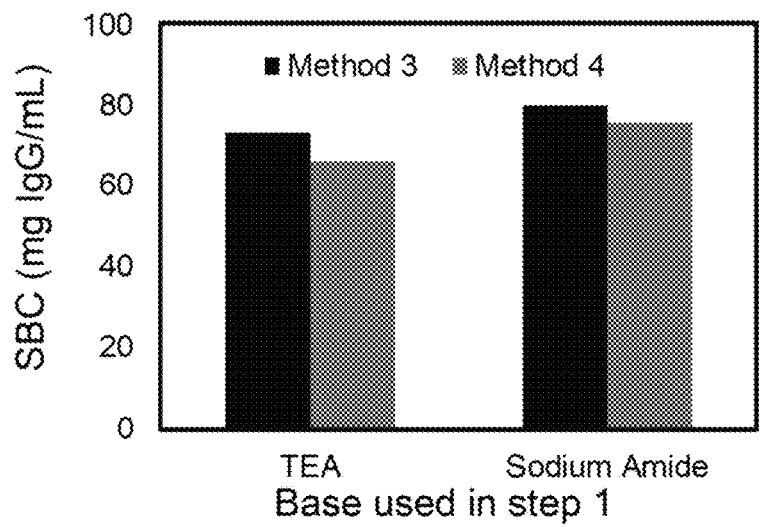
FIG. 15 shows static binding capacity of Protein A membranes prepared using Epichlorohydrin and further modified using Methods 3 and 4 according to the present invention.

In FIG. 15, the membranes with pores sizes of 0.2 μm were activated in two different Epichlorohydrin solutions, each utilizing a different base catalyst. Solution A is 1.45 mg sodium amide, 0.132 mL Epichlorohydrin/mL DMSO, and Solution B is 0.067 mL TEA, 0.132 mL Epichlorohydrin/mL DMSO. Subsequently, the activated membranes were submerged into Protein A solutions using formula described in Methods 3 and 4.

Figure 16:
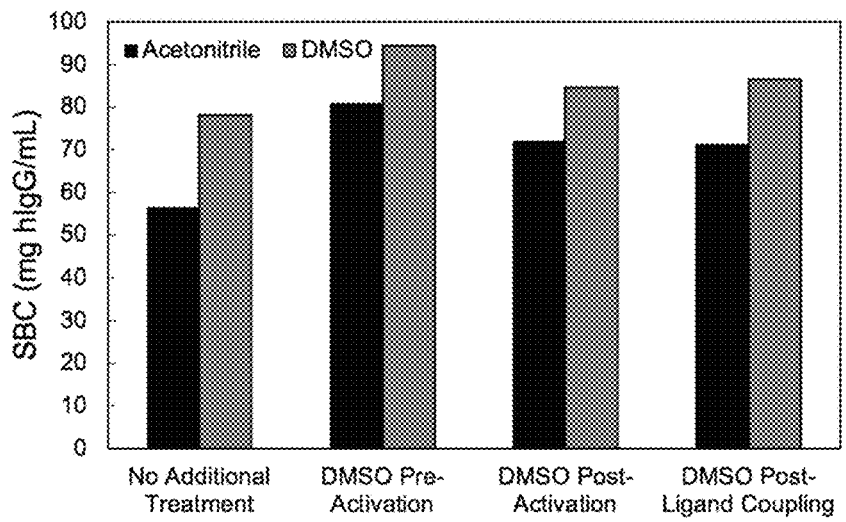
FIG. 16 shows static binding capacity of Protein A membranes with additional DMSO soaking described in Method 5 according to the present invention.

Previous examples have showed that soaking the membrane with a swelling solvent, such as DMSO, during surface activation increases binding capacity. FIG. 16 shows that binding capacity can also be increased by swelling the membrane before or after any step during affinity membrane preparation per Methods 1-4, including pre or post surface activation, and post ligand immobilization. In this example, regenerated cellulose membranes were activated in either DSC/DMSO or DSC/Acetonitrile. The Protein A coupling solution contains ~60% ethanol and 5 mg/mL Protein A in 100 mM Trisbase buffer, pH=8.0-9.0. The membranes prepared were soaked in DMSO for 15 h at 40° C. pre surface activation, post surface activation, or post ligand coupling. The results indicated that the swelling can improve binding capacity by 45% over unswollen membranes. Membranes that have undergone swelling treatments increase binding capacity by increasing exposure of reactive sites, coupling sites, or ligand sites.

Figure 17:
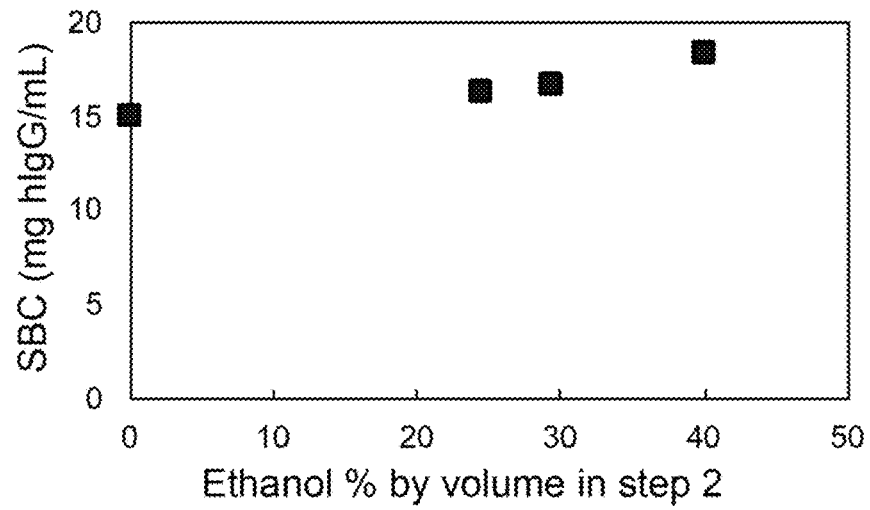
FIG. 17 shows static binding capacity of Concanavalin A membranes using different amounts of ethanol in Method 3 according to the present invention.

FIG. 17 shows the SBC of Con A membranes prepared using different amounts of ethanol (0%, 24.5%, 29.4%, and 40% ethanol by volume) in the ligand coupling step in Method 3 with ligand concentration of 5 mg/mL. hIgG was used as the test glycoprotein to measure SBC in 20 mM Tris pH 7.4, 0.5 M NaCl, 1 mM $MnCl_2$, 1 mM $CaCl_2$. SBC increases with increasing addition of ethanol. The maximum SBC in this example is obtained near the cloud point at 40% ethanol by volume.

ii: $DBC_{10\%}$ measurements: $DBC_{10\%}$ represents the mass of protein bound per unit volume of membrane bed when the protein concentration in the effluent from the membrane bed reaches 10% of the feed concentration. Membranes were packed into a plastic prototype mini column (membrane volume=0.08-0.1 mL) to measure $DBC_{10\%}$ values. The tests were conducted using an AKTA Pure chromatography system. Flow rates of 10-100 column volumes/minute (CVs/min), corresponding to residence times from 6-0.6 s, were used to measure $DBC_{10\%}$. The test solution was different concentrations of human IgG in 1× PBS buffer at pH=7.3.

Figure 18:
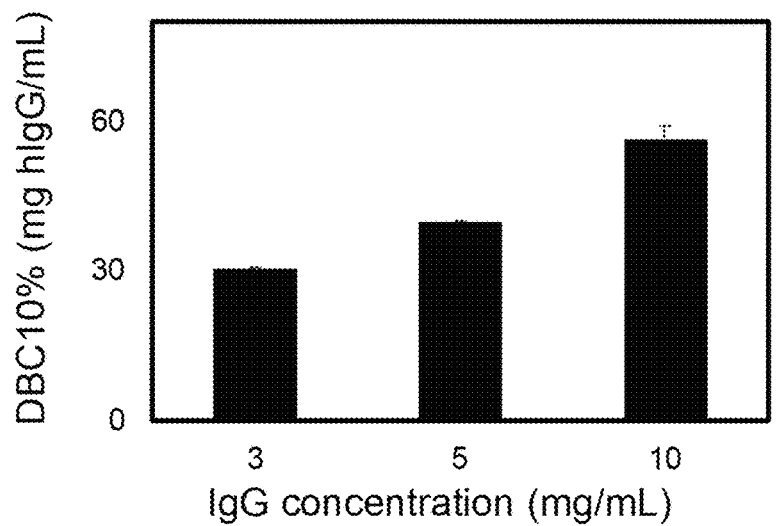
FIG. 18 shows dynamic binding capacity of Protein A membranes using Method 1 according to the present invention.

FIG. 18 shows the $DBC_{10\%}$ of the Protein A membrane packed in a syringe-filter like membrane holder. $DBC_{10\%}$ were collected using different concentrations of hIgG solutions. Data shown is the average of three runs with the error bar depicting standard error. These membranes were prepared by Method 1. Membranes with a pore size of 0.45 μm were activated in 50 mg DSC/mL DMSO solution followed by further modification in 50 uL DMEDA/mL DMSO solution followed by ligand coupling using 5 mg/mL Protein A in 20 mM Trisbase buffer, pH=7.0.

Figure 19:
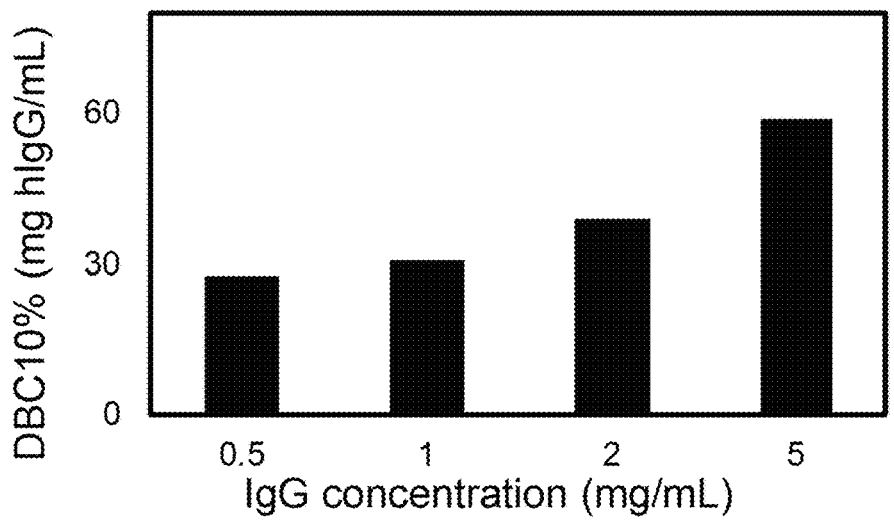
FIG. 19 shows dynamic binding capacity of Protein A membranes using Method 2 according to the present invention.

FIG. 19 shows the $DBC_{10\%}$ of the Protein A membrane packed in a syringe-filter like membrane holder. $DBC_{10\%}$ were collected using different concentrations of hIgG solutions. These membranes were prepared by Method 2. Membranes with a pore size of 0.45 μm were activated in 30 mg DSC/mL DMSO solution followed by ligand coupling using 120 mg/mL Protein A in 100 mM Trisbase buffer, pH=8.0-9.0.

Figure 20:
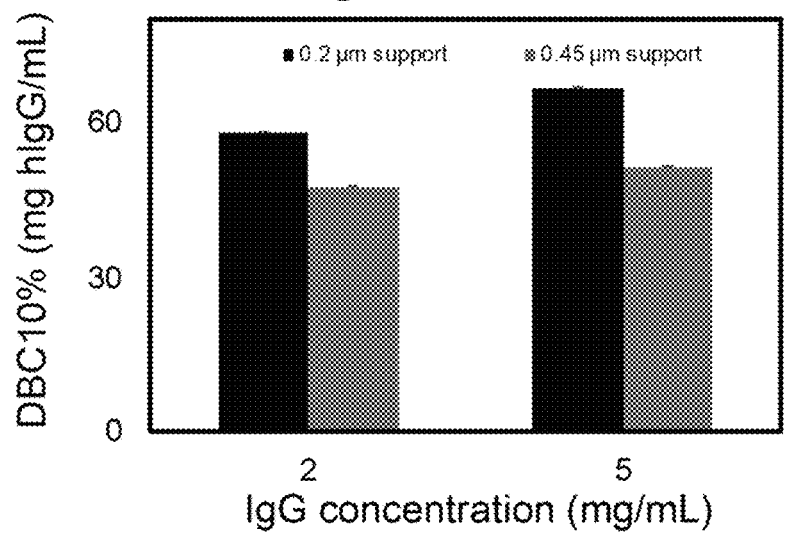
FIG. 20 shows dynamic binding capacity of Protein A membranes using Method 3 according to the present invention.

FIG. 20 shows the $DBC_{10\%}$ of the Protein A membrane packed in a syringe-filter like membrane holder. $DBC_{10\%}$ were collected using different concentrations of hIgG solutions. Data shown is the average of three runs with the error bar depicting standard error. These membranes were prepared by Method 3. Membranes with a pore size of 0.2 μm and 0.45 μm were activated separately in 5 mg DSC/mL DMSO solution followed by ligand coupling using 5 mg/mL Protein A in ~60% ethanol, 100 mM Trisbase, pH=8.0-9.0.

Figure 21:
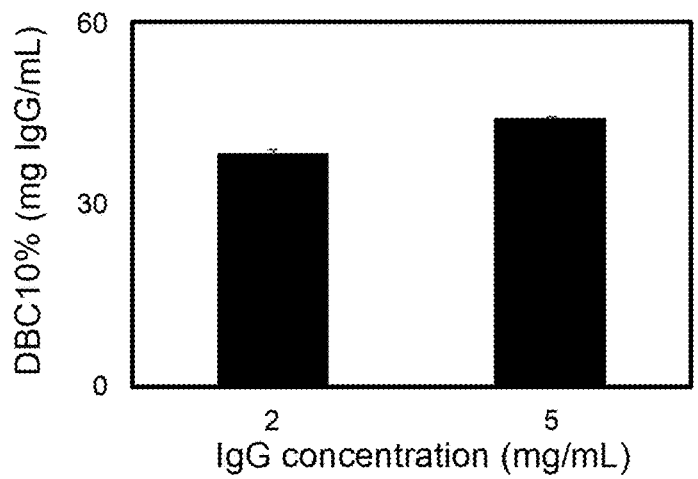
FIG. 21 shows dynamic binding capacity of Protein A membranes using Method 3 according to the present invention.

FIG. 21 shows the $DBC_{10\%}$ of Protein A membranes prepared using Method 3. Two different IgG concentrations were used at 2.32 seconds residence time. Data shown is the average of three runs with the error bar depicting standard error. Regenerated cellulose membranes with pore sizes of 0.2 μm were activated in a solution of 0.0665 mL TEA, 0.131 mL Epichlorohydrin/mL DMSO. The subsequent coupling solution contains 5 mg/mL Protein A in ~60% ethanol, 100 mM Trisbase, pH=8.0-9.0.

Figure 22:
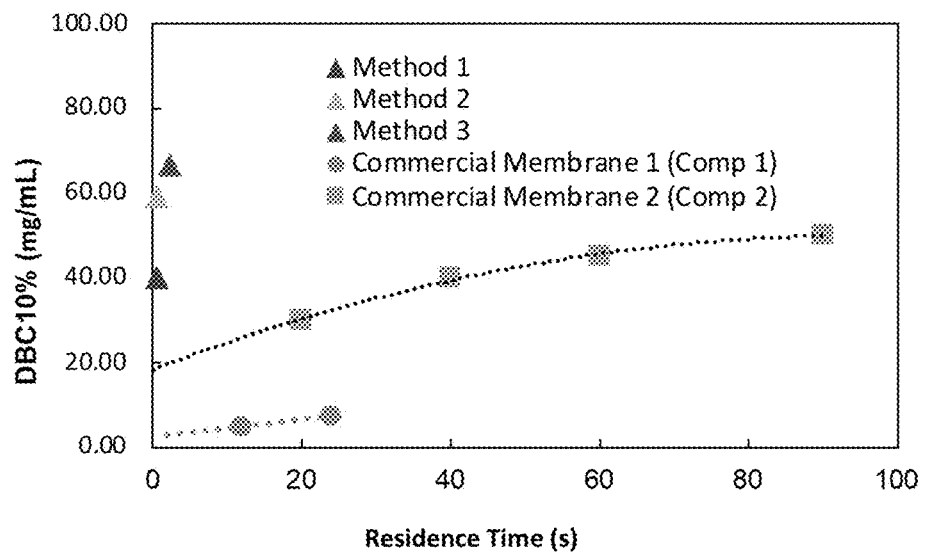
FIG. 22 shows a comparison of the membrane according to the present invention to other commercial membrane products; and, FIG. 23 shows a comparison of the membrane according to the present invention to a commercial resin product.
Figure 23:
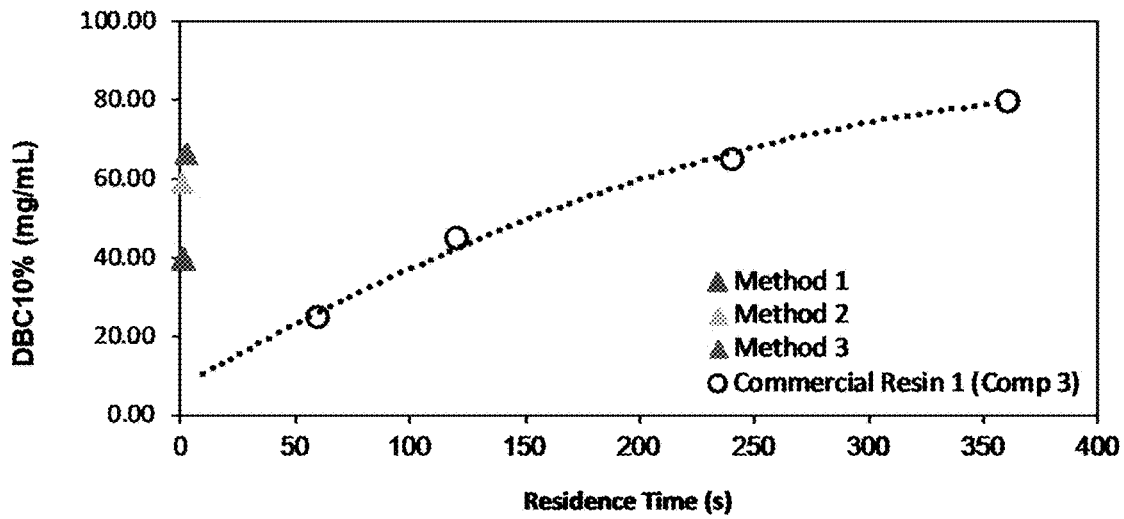

FIGS. 22 and 23 compare the performance of the Protein A membrane columns with commercial products identified as Comp 1, Comp 2 and Comp 3. The membrane prepared according to the present invention yields remarkable $DBC_{10\%}$ of 40, 54, and 66 mg hIgG/mL at 0.6-6 s residence time and significantly outperforms commercial Protein A membrane products Comp1 and Comp 2 (FIG. 22) and another Protein A resin product Comp 3 (FIG. 23). FIG. 23 compares performance with a top industry resin column, which achieves only 25 mg hIgG/mL at 60 s residence time.

Table 2 illustrates the effect of different treatments on specific surface area (SSA) in square meters relative to volume of membrane in mL on regenerated cellulose membranes. Data was derived from BET analysis.

TABLE 2

Specific surface area per volume membrane (m^2/mL) of membranes treated with combinations of DSC, DMSO, and acetonitrile.

| Membrane | SSA (m^2/mL) |
| --- | --- |
| 1 μm support no treatment | 1.532 |
| 0.45 μm support no treatment | 3.596 |
| 0.2 μm support no treatment | 5.118 |
| 0.2 μm support treated with DMSO only | 7.387 |
| 0.2 μm support treated with DSC and DMSO | 8.354 |
| 0.2 μm support treated with DSC and Acetonitrile | 7.431 |

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A method for preparing an adsorptive media for binding biologic molecules, the method comprising:
 immersing a macroporous support in a first solution comprising a coupling reagent and a first solvent for attachment of said coupling reagent to form coupling groups on the macroporous support;
 immersing said macroporous support in an incubating solution to couple a molecule having an affinity to a biological target to at least a portion of said coupling groups, the incubating solution comprising:
 water;
 an organic solvent present in an amount ranging from 90% to 110% of a volumetric amount of the organic solvent at the cloud point of the ligand; and
 the molecule comprising a nucleotide, an oligonucleotide, a peptide, a polypeptide, a protein, or any combination thereof.

2. The method of claim 1 wherein said macroporous support is selected from the group consisting of polyolefins membranes, polyethersulfone membranes, poly(tetrafluoroethylene) membranes, nylon membranes, fiberglass membranes, hydrogel membranes, hydrogel monoliths, polyvinyl alcohol membranes, natural polymer membranes, cellulose ester membranes, cellulose acetate membranes, regenerated cellulose membranes, cellulosic nanofiber membranes, cellulosic monoliths, filter paper membranes, macroporous support membranes comprising cellulose or a derivative of cellulose, and combinations thereof.

3. The method of claim 1 wherein the macroporous support is immersed in a swelling solvent solution to swell said macroporous support and increase exposure of at least one of reactive sites, the coupling groups, and ligand sites during preparation of the adsorptive media.

4. The method of claim 3 wherein said swelling solvent solution comprises at least one swelling solvent selected from the group consisting of dimethyl sulfoxide (DMSO), a mixture of DMSO and other solvents in which the DMSO content is greater than 70% by volume, organic solvents, hexamethylphosphoramide, ionic liquids, sulfolane, and combinations thereof.

5. The method of claim 1 wherein said coupling reagent is selected from the group consisting of N,N'-disuccinimidyl carbonate (DSC), 1,1'-carbonyldiimidazole (CDI), N,N'-dicyclohexylcarbodiimide (DCC), 1-ethyl-3-(3-dimethylaminopropyl)carbodiimide hydrochloride) (EDC), cyanogen halides, diisocyanates, diglycidyl ethers, epichlorohydrin, tosyl chloride, glutaraldehyde, divinyl sulfone, acyl halides, triazines, anhydrides, and combinations thereof.

6. The method of claim 1 wherein said organic solvent is selected from the group consisting of water-miscible alcohols, ketones, ethers, amides, and combinations thereof.

7. The method of claim 6 wherein said organic solvent comprises methanol, ethanol, 1-propanol, 2-propanol, 1-butanol, 2-butanol, acetonitrile, acetone, tetrahydrofuran (THF), dimethylformamide (DMF), dimethylsulfoxide (DMSO), or any combination thereof.

8. The method of claim 1 wherein said first solvent comprises dimethyl sulfoxide (DMSO);
 said coupling reagent comprises N,N'-disuccinimidyl carbonate (DSC);
 the organic solvent of the incubating solution comprises methanol, ethanol, 1-propanol, 2-propanol, 1-butanol, 2-butanol, acetonitrile, acetone, tetrahydrofuran (THF), dimethylformamide (DMF), dimethylsulfoxide (DMSO), or any combination thereof; and
 said ligand comprises Protein A at a concentration of 10 mg/ml or less.

9. The method of claim 1, wherein the molecule is present in the incubating solution at a concentration of 0.1 mg/mL to 45 mg/mL.

10. The method of claim 1, wherein the molecule comprises Protein A.

11. The method of claim 1, wherein the incubating solution comprises a buffer.

12. The method of claim 11, wherein the buffer comprises Trisbase, phosphate, or carbonate.

13. The method of claim 1, wherein the incubating solution has a pH between 6.0 and 10.0.

14. The method of claim 1, wherein the adsorptive media exhibits a dynamic binding capacity (DBC) of 20 mg to 90 mg of human Immunoglobulin G per milliliter at a residence time of 6 s or shorter with 3 bar or less backpressure.

15. A method for preparing adsorptive media, the method comprising:
 contacting a macroporous support with a first solution comprising a coupling agent and a first solvent to form a macroporous support having coupling groups; and
 contacting the macroporous support having coupling groups with an incubating solution comprising water, an organic solvent, and a molecule having an affinity to a biological target to couple the ligand with at least some of the coupling groups,
 wherein the organic solvent is present in the incubating solution in an amount ranging from 75% to 125% of amount of organic solvent at a cloud point of the ligand, and
 wherein the molecule comprises a nucleotide, an oligonucleotide, a peptide, a polypeptide, a protein, or any combination thereof.

16. The method of claim 15, wherein the molecule is present in the incubating solution at a concentration of 0.1 mg/mL to 45 mg/mL.

17. A method for preparing adsorptive media, the method comprising:
 contacting a macroporous cellulose membrane with a first solution comprising a coupling agent and a first solvent to form a macroporous cellulose membrane having coupling groups; and
 contacting the macroporous cellulose membrane having coupling groups with an incubating solution comprising water, an organic solvent, and a molecule having an affinity to a biological target to couple the molecule with at least some of the coupling groups,
 wherein the organic solvent is present in the incubating solution in an amount ranging from 50 vol-% to 99 vol %, and
 wherein the molecule comprises a nucleotide, an oligonucleotide, or any combination thereof.

18. The method of claim 17, wherein the molecule is oligodeoxythymidine.

19. The method of claim 17, wherein organic solvent is present in the incubating solution in an amount of 74 vol-% to 99 vol-%.

* * * * *